(12) United States Patent
Cohen et al.

(10) Patent No.: US 10,675,293 B2
(45) Date of Patent: Jun. 9, 2020

(54) NUCLEOSIDE AGENTS FOR THE REDUCTION OF THE DELETERIOUS ACTIVITY OF EXTENDED NUCLEOTIDE REPEAT CONTAINING GENES

(71) Applicants: The Board of Trustees of the Leland Stanford Junior University, Stanford, CA (US); National Yang-Ming University, Taipei (TW)

(72) Inventors: Stanley N. Cohen, Stanford, CA (US); Ning Deng, Palo Alto, CA (US); Yanan Feng, San Jose, CA (US); Tzu-Hao Cheng, Taipei (TW); Yun-Yun Wu, Taipei (TW); Wen-Chieh Hsieh, Taipei (TW)

(73) Assignees: The Board of Trustees of the Leland Stanford Junior University, Stanford, CA (US); National Yang-Ming University, Taipei (TW)

( * ) Notice: Subject to any disclaimer, the term of this patent is extended or adjusted under 35 U.S.C. 154(b) by 0 days.

(21) Appl. No.: 15/554,679

(22) PCT Filed: May 18, 2016

(86) PCT No.: PCT/US2016/033116
§ 371 (c)(1),
(2) Date: Aug. 30, 2017

(87) PCT Pub. No.: WO2016/196012
PCT Pub. Date: Dec. 8, 2016

(65) Prior Publication Data
US 2018/0064744 A1 Mar. 8, 2018

Related U.S. Application Data

(60) Provisional application No. 62/168,558, filed on May 29, 2015.

(51) Int. Cl.
| | |
|---|---|
| *A61K 31/7076* | (2006.01) |
| *C12N 15/113* | (2010.01) |
| *G01N 33/50* | (2006.01) |
| *A61K 31/7064* | (2006.01) |
| *A61K 48/00* | (2006.01) |

(52) U.S. Cl.
CPC ...... *A61K 31/7076* (2013.01); *A61K 31/7064* (2013.01); *C12N 15/113* (2013.01); *G01N 33/50* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 6,258,795 B1 | 7/2001 | Von Borstel et al. | |
| 6,472,378 B2 | 10/2002 | Von Borstel | |
| 6,956,028 B2 | 10/2005 | Von Borstel | |
| 7,582,619 B2 | 9/2009 | Von Borstel | |
| 7,638,501 B1 | 12/2009 | Naviaux | |
| 7,807,654 B2 | 10/2010 | Von Borstel et al. | |
| 7,915,233 B1 | 3/2011 | Von Borstel | |
| 8,067,392 B2 | 11/2011 | Von Borstel | |
| 8,569,254 B2 | 10/2013 | Cheng et al. | |
| 8,598,141 B2 | 12/2013 | Haydon et al. | |
| 8,748,408 B2 | 6/2014 | Naviaux | |
| 9,211,303 B2 | 12/2015 | Cheng et al. | |
| 9,226,935 B2 | 1/2016 | Cheng et al. | |
| 2001/0025032 A1* | 9/2001 | Von Borstel | A61K 31/513 514/50 |
| 2005/0020521 A1 | 1/2005 | Rana | |
| 2005/0096284 A1 | 5/2005 | McSwiggen | |
| 2006/0270623 A1 | 11/2006 | McSwiggen | |
| 2006/0276527 A1* | 12/2006 | Tidmarsh | A61K 31/11 514/406 |
| 2007/0105803 A1 | 5/2007 | Manoharan et al. | |
| 2007/0174924 A1 | 7/2007 | Allen | |
| 2008/0070246 A1 | 3/2008 | Cheng et al. | |

(Continued)

FOREIGN PATENT DOCUMENTS

| | | |
|---|---|---|
| WO | WO199518616 A2 | 7/1995 |
| WO | WO 2004/041838 A1 | 5/2004 |

(Continued)

OTHER PUBLICATIONS

Pasternack et al., The Journal of Biological Chemistry, vol. 234(11):2992-2997, Nov. 1959.*

(Continued)

*Primary Examiner* — Sean McGarry
(74) *Attorney, Agent, or Firm* — Bret E. Field; Bozicevic, Field & Francis LLP

(57) ABSTRACT

Aspects of the invention include methods of reducing the deleterious activity of a mutant extended nucleotide repeat (NR) containing target gene in a cell by contacting the cell with an effective amount of a nucleoside agent, as well as compositions used in such methods. The deleterious activity (e.g., toxicity and/or dis-functionality of products encoded thereby) of a mutant extended NR containing target gene may be reduced in a variety of different ways, e.g., by reducing (and in some instances differentially, including selectively, reducing) the production or activity of toxic expression products (e.g., RNA or protein) encoded by the target gene. Kits and compositions for practicing the subject methods are also provided.

20 Claims, 14 Drawing Sheets

(56) References Cited

U.S. PATENT DOCUMENTS

| | | |
|---|---|---|
| 2008/0176812 A1 | 7/2008 | Davidson et al. |
| 2008/0176816 A1 | 7/2008 | Chern |
| 2008/0318884 A1 | 12/2008 | Detloff et al. |
| 2011/0172291 A1 | 7/2011 | Aronin et al. |
| 2012/0277178 A1 | 11/2012 | Jin et al. |
| 2013/0059902 A1 | 3/2013 | Corey et al. |
| 2013/0331437 A1 | 12/2013 | Cheng et al. |
| 2015/0159155 A1 | 6/2015 | Hung et al. |

FOREIGN PATENT DOCUMENTS

| | | |
|---|---|---|
| WO | WO2005009349 A2 | 2/2005 |
| WO | WO 2005/027980 A1 | 3/2005 |
| WO | WO2006133353 A1 | 12/2006 |
| WO | WO 2011/016840 A2 | 2/2011 |
| WO | WO2012064340 A1 | 5/2012 |
| WO | WO 2012/078906 A2 | 6/2012 |
| WO | WO2015061426 A1 | 4/2015 |

OTHER PUBLICATIONS

Naguib et al., Cell Reports vol. 26:45-53, Jan. 2, 2019.*

Gomes-Pereira, "Chemically induced increases and decreases in the rate of expansion of a CAG{middle dot}CTG triplet repeat", Nucleic Acids Research, vol. 32, No. 9, May 17, 2004 (May 17, 2004), pp. 2865-2872.

Hartzog, et al., 'The Spt4-Spt5 complex: a multi-faceted regulator of transcription elongation', Biochim Biophys Acta. Jan. 2013;1829 (1), pp. 105-115.

Mievis, et al. "Citicoline is not protective in experimental models of Huntington's disease",Neurobiology of Aging, vol. 28, No. 12, Dec. 1, 2007 (Dec. 1, 2007), pp. 1944-1946. Abstract Only.

Apostol et al. "A cell-based assay for aggregation inhibitors as therapeutics of polyglutamine-repeat disease and validation in *Drosophila*", Proc. Natl. Acad. Sci. USA. (May 2003), 100(10):5950-5.

Chen et al. "DSIF, the Paf1 complex, and Tat-SF1 have nonredundant, cooperative roles in RNA polymerase II elongation", Genes & Development (2009) 23: 2765-2777.

Cheng et al. "Effects on murine behavior and lifespan of selectively decreasing expression of mutant huntingtin allele by supt4h knockdown," PLoS Genetics, Mar. 11, 2015, vol. 11, No. 3, pp. e1005043 1-17.

Cummings et al. "Fourteen and counting: unraveling trinucleotide repeat diseases", Human Molecular Genetics (Apr. 2000), 9(6):909-916.

Difiglia et al. "Therapeutic silencing of mutant huntingtin with siRNA attenuates striatal and cortical neuropathology and behavioral deficits", Proc. Natl. Acad. Sci. USA. (Oct. 2007), 104(43):17204-9.

Furling et al. "Viral vector producing antisense RNA restores myotonic dystrophy myoblast functions", Gene Ther. (May 2003), 10(9):795-802.

Gorbunova et al. "Genome-wide demethylation destabilizes CTG. CAG trinucleotide repeats in mammalian cells", Human Molecular Genetics (Dec. 2004), 13(23):2979-2989.

Helene et al. "Specific regulation of gene expression by antisense, sense and antigene nucleic acids", Biochimica et Biophysica Acta, vol. 1049 (1990), pp. 99-125.

Hu et al. "Allele-specific silencing of mutant huntingtin and ataxin-3 genes by targeting expanded CAG repeats in mRNAs", Nat. Biotechnol. (May 2009), 27(5):478-84.

Liu et al. "Spt4 Is Selectively Required for Transcription of Extended Trinucleotide Repeats", Cell (Feb. 2012), 148(4):690-701.

Omi et al. "14-3-3zeta is indispensable for aggregate formation of polyglutamine-expanded huntingtin protein", Neurosci Lett. (Jan. 2008), 431(1):45-50.

Sánchez et al. "Pivotal role of oligomerization in expanded polyglutamine neurodegenerative disorders", Nature (Jan. 2003), 421(6921):373-9.

Saydoff et al. "Oral uridine pro-drug PN401 is neuroprotective in the R6/2 and N171-82Q mouse models of Huntington's disease," Neurobiology of Disease 24 (2006) 455-465.

Sims et al. "Elongation by RNA polymerase II: the short and long of it", Genes & Development (2004) 18:2437-2468.

Wang et al. "Clinico-pathological rescue of a model mouse of Huntington's disease by siRNA", Neurosci Res. (Nov. 2005), 53(3):241-9.

Wellstat Therapeutics Corporation, Xuriden™ Highlights of Prescribing Information and Instructions for Use, Sep. 2015, 24 pages.

Wu et al. "NELF and DSIF cause promoter proximal pausing on the hsp70 promoter in *Drosophila*", Genes & Development (2003) 17:1402-1414.

Pasternak, et al. The biochemical activity of 6-azauridine: interference with pyrimidine metabolism in transplantable mouse tumors. J Biol Chem, Nov. 1959, vol. 234, No. 11, pp. 2992-2997.

* cited by examiner (C)

(D)

(B)

(C)

A

B

C

D

Mutational interference with luciferase signal produced by Supt4h/5h interaction

HD101

HD103

HD106

HD107

A

B 24 hours after transfection 48 hours after transfection

A

B

NUCLEOSIDE AGENTS FOR THE REDUCTION OF THE DELETERIOUS ACTIVITY OF EXTENDED NUCLEOTIDE REPEAT CONTAINING GENES

CROSS-REFERENCE TO RELATED APPLICATIONS

Pursuant to 35 U.S.C. § 119 (e), this application claims priority to the filing date of the U.S. Provisional Patent Application Ser. No. 62/168,558, filed May 29, 2015, the disclosure of which is incorporated herein by reference.

GOVERNMENT RIGHTS

This invention was made with Government support under contracts NS085812 and TR001085 awarded by the National Institutes of Health. The Government has certain rights in the invention.

INTRODUCTION

In the past few decades, abnormal expansion of nucleotide repeats in coding or non-coding DNA regions have been associated with many disease conditions. These mutant regions of expanded repeats may result in mutant gene products that cause disease through a variety of different mechanisms, e.g., loss- or gain-of-function mechanisms, e.g., as a result of toxic RNA, altered RNA processing, misfolded and abnormal proteins, reduced gene expression and altered protein function (Cummings and Zoghbi, "Fourteen and counting: unraveling trinucleotide repeat diseases," Human Molecular Genetics (2000) 9: 909-16).

Long repeats may form unusual DNA structures that can increase the likelihood of expansion or sometimes contraction. Such structures comprise hairpins in single-stranded DNA, triplex DNA, quadruplex DNA, parallel-strand DNA, and unwound DNA (Sinden, et al., "Mechanisms of DNA Repeat Expansion," Nucleic Acids and Molecular Biology (2006) 19: 3). Models explaining the dynamic behavior of repeat regions also involve slipped strand mispairing during DNA replication or repair, misalignment and excision repair, and unequal crossing-over (Zoghbi, "Trinucleotide Repeat Disorders," Principles of Molecular Medicine (2006) 1114-1122). Due to somatic and germline instability of the repeat regions, families with repeat mutations may see an increase in disease severity and an earlier age of onset from one generation to the next, a phenomenon known as anticipation. Anticipation generally correlates with larger repeat lengths in the next generation, and paternal transmissions carry a greater risk of expansion (Cummings and Zoghbi, "Fourteen and counting: unraveling trinucleotide repeat diseases," Human Molecular Genetics (2000) 9: 909-16).

Certain trinucleotide repeat diseases result from repeats occurring in non-coding sequences, and such repeats may results in loss of function of the affected gene. Trinucleotide repeat sequences implicated in diseases include CGG, GCC, GAA, CTG, and CAG units. The nature of the sequence itself and the location of repeats can affect the mechanism of disease pathogenesis. X-linked trinucleotide diseases are Fragile X syndrome (FRAXA), Fragile XE MR (FRAXE) and Fragile X tremor/ataxia syndrome (FXTAS). This group of diseases includes both loss of function mutations and the production of toxic RNA. Autosomal diseases include myotonic dystrophy, Friedreich's ataxia and two types of spinocerebellar ataxia (SCA8 and SCA12)(Cummings and Zoghbi, "Fourteen and counting: unraveling trinucleotide repeat diseases," Human Molecular Genetics (2000) 9: 909-16). Phenotypic manifestations of a disease are highly variable, and pathogenic mechanisms also vary from disease to disease (Cummings and Zoghbi, "Fourteen and counting: unraveling trinucleotide repeat diseases," Human Molecular Genetics (2000) 9: 909-16).

Polyglutamine repeat diseases are a particular trinucleotide repeat disease category. These diseases result from exonic repeats that are located in protein-coding regions of genes and code for polyglutamine tracts in the proteins encoded by these genes. Subsets of neurons are especially vulnerable to polyglutamine repeat disease mechanisms (Cummings and Zoghbi, "Fourteen and counting: unraveling trinucleotide repeat diseases," Human Molecular Genetics (2000) 9: 909-16), (Blum, et al., "PolyQ disease: misfiring of a developmental cell death program," Trends in Cell Biology (2013) 23: 168-74). The following examples are known polyglutamine repeat diseases: Dentatorubral-pallidoluysian atrophy (DRPLA), Huntington's disease, spinobulbar muscular dystrophy, and spinocerebellar ataxia types 1, 2, 3, 6, 7, and 17. Studies also suggest that Huntington's Disease-like 2 may result from pathogenic polyglutamine repeat mechanisms (Wilburn, et al., "An antisense CAG repeat transcript at JPH3 locus mediates expanded polyglutamine protein toxicity in Huntington's disease-like 2 mice," Neuron (2011) 70: 427-40).

Polyglutamine repeat diseases commonly produce symptoms that have an onset relatively late in life and lead to progressive neuronal dysfunction and ultimately, to severe neurodegeneration (Cummings and Zoghbi, "Fourteen and counting: unraveling trinucleotide repeat diseases," Human Molecular Genetics (2000) 9: 909-16). A hallmark of these diseases is the presence of aggregates of proteins containing polyglutamine tracts, mainly found in the nucleus of affected neurons (Cummings and Zoghbi, "Fourteen and counting: unraveling trinucleotide repeat diseases," Human Molecular Genetics (2000) 9: 909-16). Misfolded repeat containing proteins may be toxic, and protein aggregates may have altered interactions with transcriptional regulators. However, the exact pathogenic mechanism is complex. Not only do repeat expansions affect genes encoding proteins with dissimilar functions, but polyglutamine repeat diseases can also manifest in different regions of the brain (Blum, et al., "PolyQ disease: misfiring of a developmental cell death program," Trends in Cell Biology (2013) 23: 168-74). Other studies show polyglutamine repeat proteins may play a role in inappropriately activating a cell's apoptotic pathway, leading to cell death (Cummings and Zoghbi, "Fourteen and counting: unraveling trinucleotide repeat diseases," Human Molecular Genetics (2000) 9: 909-16), (Blum, et al., "PolyQ disease: misfiring of a developmental cell death program," Trends in Cell Biology (2013) 23: 168-74).

Nucleotide repeats encoding polyalanine tracts have also been found to cause disease. For example trinucleotide repeats encoding alanine tracts have been linked to congenital malformation syndromes (Albrecht and Mundlos, "The other trinucleotide repeat: polyalanine expansion disorders," Current Opinion in Genetics & Development (2005) 285-93). Affected genes encode transcription factors that play roles during development, and the repeats lead to misfolded proteins and protein aggregation and degradation (Albrecht and Mundlos, "The other trinucleotide repeat: polyalanine expansion disorders," Current Opinion in Genetics & Development (2005) 285-93). Unstable regions of various other sizes of nucleotide repeat units are also the basis for disease. Tetranucleotide repeats cause myotonic dystrophy type 2, and pentanucleotide repeats result in SCA 10 and SCA 31.

Dodecamer repeats have been implicated in progressive myoclonic epilepsy (Zoghbi, "Trinucleotide Repeat Disorders," Principles of Molecular Medicine (2006) 1114-1122), (Sato, et al., "Spinocerebellar Ataxia Type 31 is Associated with "Inserted" Penta-Nucleotide Repeats Containing (TGGAA)n," The American Journal of Human Genetics (2009) 85: 544-57), (Matsuura, et al., "Large expansion of the ATTCT pentanucleotide repeat in spinocerebellar ataxia type 10," Nature Genetics (2000) 26: 191-94), (Clark, "Introduction to Trinucleotide Repeat Diseases," Neurodegeneration: The Molecular Pathology of Dementia and Movement Disorders (2011) 255-256).

Expansion of trinucleotide repeats in gene segments that do not encode proteins can cause disease by producing abnormal RNAs. Furthermore, repeat expansions need not necessarily involve trinucleodites. For example, expansion of the GGGGCC hexanucleotide repeat in non-coding regions of C9ORF72 is the most common cause of two diseases, autosomal-dominant frontotemporal dementia (FTD) and amyotrophic lateral sclerosis (ALS). Individuals afflicted with this autosomal dominant mutation experience deficits in executive function and behavioral changes (FTD) or motor neuron dysfunction (ALS). Some patients may have a combination of FTD and ALS symptoms (Renton, et al., "A Hexanucleotide Repeat Expansion in C9ORF72 is the Cause of Chromosome 9p21-Linked ALS-FTD," Neuron (2011) 72: 257-68), (Yokoyama, et al., "C9ORF72 hexanucleotide repeats in behavioral and motor neuron disease: clinical heterogeneity and pathological diversity," American Journal of Neurodegenerative Disease (2014) 3: 1-18). C9ORF72 hexanucleotide repeats are also rarely associated with parkinsonism, pseudodementia, psychiatric disorders, and other neurological diseases (Bieniek, et al., "Expanded C9ORF72 hexanucleotide repeat in depressive pseudodementia," JAMA Neurology (2014) 71: 775-81), (Yokoyama, et al., "C9ORF72 hexanucleotide repeats in behavioral and motor neuron disease: clinical heterogeneity and pathological diversity," American Journal of Neurodegenerative Disease (2014) 3: 1-18).

While the number of hexanucleotide repeats in C9ORF72 normally is fewer than 25, mutant repeat regions can contain up to 1500 or more hexanucleotide units (DeJesus-Hernandez, et al., "Expanded GGGGCC Hexanucleotide Repeat in Noncoding Region of C9ORF72 Causes Chromosome 9p-Linked FTD and ALS," Neuron (2011) 72: 245-56). Studies propose that the hexanucleotide repeat regions are unstable and that abnormally long repeats may occur on a predisposing haplotypic background prone to expansion (DeJesus-Hernandez, et al., "Expanded GGGGCC Hexanucleotide Repeat in Noncoding Region of C9ORF72 Causes Chromosome 9p-Linked FTD and ALS," Neuron (2011) 72: 245-56), (Renton, et al., "A Hexanucleotide Repeat Expansion in C9ORF72 is the Cause of Chromosome 9p21-Linked ALS-FTD," Neuron (2011) 72: 257-68), (Fratta, et al., "Screening a UK amyotrophic lateral sclerosis cohort provides evidence of multiple origins of the C9ORF72 expansion," Neurobiology of Aging (2015) 36: 546. e1-7). It is not completely clear whether anticipation is a characteristic of GGGGCC hexanucleotide repeat diseases (DeJesus-Hernandez, et al., "Expanded GGGGCC Hexanucleotide Repeat in Noncoding Region of C9ORF72 Causes Chromosome 9p-Linked FTD and ALS," Neuron (2011) 72: 245-56), (Renton, et al., "A Hexanucleotide Repeat Expansion in C9ORF72 is the Cause of Chromosome 9p21-Linked ALS-FTD," Neuron (2011) 72: 257-68). As techniques for measuring repeats develop beyond Southern blotting, the somatic instability and methylation state of the repeat itself and surrounding regions needs further investigation (Fratta, et al., "Screening a UK amyotrophic lateral sclerosis cohort provides evidence of multiple origins of the C9ORF72 expansion," Neurobiology of Aging (2015) 36: 546. e1-7).

SUMMARY

Aspects of the invention include methods of reducing the deleterious activity of a mutant extended nucleotide repeat (NR) containing target gene in a cell by contacting the cell with an effective amount of a nucleoside agent, as well as compositions used in such methods. The deleterious activity (e.g., toxicity and/or dis-functionality of products encoded thereby) of a mutant extended NR containing target gene may be reduced in a variety of different ways, e.g., by reducing (and in some instances differentially, including selectively, reducing) the production or activity of toxic expression products (e.g., RNA or protein) encoded by the target gene. Kits and compositions that find use in practicing the subject methods are also provided.

BRIEF DESCRIPTION OF THE DRAWINGS

The skilled artisan will understand that the drawings, described below, are for illustration purposes only. The drawings are not intended to limit the scope of the present teachings in any way.

(FIG. 2A) Schematic diagram that shows the underlying mechanism of BiFC. Fluorescent protein YFP is divided into the N-terminal (YN) and C-terminal (YC) parts. The YFP protein fragments cannot complement by themselves to produce a fluorescent signal until the complex formation is stimulated by a pair of interacting proteins that bring YN and YC together, leading to the generation of fluorescent signal. (FIG. 2B) HeLa cells, transfected with indicated plasmid constructs, were monitored under fluorescence microscope. DIC: phase contrast imaging. Supt5h NGN was in-frame fused with the YN to yield NGN-YN, while Supt4h was fused to the YC for the generation of Supt4h-YC. Supt4h(S69L) has a serine to leucine substitution at the amino acid position 69, which prevents its interaction with Supt5h. (FIG. 2C) The fluorescent signal of samples from complementary and non-complementary pairs of BiFC was assessed by a plate reader with a setting of excitation and emission wavelength at 488 and 527 nm respectively.

(FIG. 3A) Schematic diagram showing the induction of protein(s) by doxycycline in 2-PN4 and 21-VS cells. 2-PN4 expresses both Supt4h-YC and Supt5h/NGN-YN, and produces YFP fluorescence signal via YN/YC complementation. 21-VS, expressing an intact fluorescent protein Venus, is included as a control cell line. (FIG. 3B) Indicated cells were transfected with plasmid construct expressing Supt4h-YN or empty vector NIS, and then cultured in a growth medium containing doxycycline to induce the expression of NGN-YN and Supt4h-YC. Each sample was monitored by fluorescence microscope, and phase contrast imaging is included and shown in the corner of photo (left). The fluorescence intensity was assessed using MetaMorph software. The level of fluorescence in NIS-transfected samples was set to 1, and relative YFP fluorescence level in cells transfected with Supt4h-YN is shown (right).

(FIG. 4A) 2-PN4 and 21-VS cells were cultured in growth medium containing Doxycycline (4 µg/ml) and various concentrations of 6CR for 24 hours. The cell imagines were monitored by fluorescence microscope and quantified by Metamorph software. Compared to mock control, relative fluorescence intensity in cells treated with 6CR is indicated (n=3; *, p<0.05; **, p<0.01 by Student's t test). (FIG. 4B) Supt4h-YC and NGN-YN protein levels were assessed by Western blot analysis in 2-PN4 cells treated with 6CR. HA-Venus protein level was also analyzed in 21-VS cells; α-Tubulin served as a loading control. (FIG. 4C) Protein lysates, collecting from 2-PN4 cells treated with DMSO (mock control) or 20 uM 6CR, were subjected to immuno-precipitation. HA-tagged Supt4h-YC protein was precipitated using antibody against HA-epitope, and then analyzed its interaction with Flag-tagged NGN-YN by Western blot using anti-Flag antibody. (FIG. 4D) Htt gene expression was assessed by RT-PCR in 6CR-treated samples. After normalization using U6, the mRNA level was compared to mock control. Hdh$^{Q7/Q7}$ and Hdh$^{Q111/Q111}$ are murine striatal cell lines having homozygous wild-type and mutant Htt allele respectively.

(FIG. 5A) 2-PN4 and 21-VS cells were cultured in growth medium containing Doxycycline (4 µg/ml) and various concentrations of 6-AZA for 24 hours. Acquisition of imagines and quantification of fluorescence intensity were carried out as described in FIG. 3A. The fluorescence intensity in mock control was set to 1, and relative fluorescence intensity in cells treated with 6-AZA is shown in bottom panel. (FIG. 5B) Supt4h-YC and NGN-YN or HA-Venus protein level was analyzed by Western blot in 6-AZA-treated cells. α-Tubulin served as a loading control. (FIG. 5C) Htt gene expression was assessed by RT-PCR in 6-AZA-treated samples. After 18S rRNA normalization, the mRNA level was compared to mock control. Murine striatal cell lines Hdh$^{Q7/Q7}$ and Hdh$^{Q111/Q111}$ possess homozygous allele of wild-type Htt and mutant Htt respectively.

(FIG. 6A) Schematic diagram that shows the mechanism of Supt4h-NGN interaction mediated Gausssia luciferase (GLuc) activity. Gaussia luciferase is the smallest known coelenterazine-using luciferase. Human genes encoding the Supt4h protein or the amino terminal domain of Supt5h (NGN) were each fused with genes that encode subunits (GLuc1 or GLuc2) of Gaussia princeps luciferase to generate Supt4h-GL1 and NGN-GL2. The split GLuc cannot produce activity unless GLuc1 and Gluc2 was brought together by the complex formation between Supt4h and NGN I. (FIG. 6B) The RheoSwich system which is an inducible gene expression system showing little or no basal expression in the absence of inducer, RheoSwitch ligand (RSL1), but with high induction when RSL1 is present. The system contains two plasmids. The RSL1 receptor, carried by pNEBR-R1, is a heterodimer consists of Rheovreceptor 1 and Rheo activator. The gene of interest can be constructed to the 3' end to the RSL1 response promoter in pNEBR-X1. When the two plasmids are introduced into cells, the expression of gen-of-interest can be fast induced by adding RSL1 into cell culture media. In our study, the constructs of Supt4h-GL1 and NGN-GL2 were made bidirectional under RheoSwitch responsive element control in pNEBR-X1, and the addition of RSL1 can simultaneously trigger the expression of Supt4h-GL1 and NGN-GL2 in similar expression level. (FIG. 6C) The graph depicts cellular luciferase activity only resulting from the interaction of Supt4h-GLuc1 and NGN-GLuc2. The two constructs, pNEBR-X1Supt4h-GLuc1 and pNEBRX1-NGN-GLuc2, when separately introduced into cell with pNEBR-R1, show minimum level of luciferase activity with or without RSL1. High luciferase activity can only be detected when the three plasmids were cotransfected into cells in the presence of RSL1. (FIG. 6D) The luciferase activity is specific to and dependent on the interaction between Supt4h and NGN. HEK293 cells were transfected with pNEBR-R1 plus indicated plasmids. Significantly increasing luciferase activity is detected when the fusion proteins bind to each other. Non-interacting Gluc components were unable to produce luciferase activity in the absence of interaction. One point mutation on NGN (S214F on human Supt5h, corresponding to S324F on yeast Spt5), which inhibits formation of a Supt4h/5h complex, completely abolished the luciferase activity mediated by Supt4h/NGN interaction.

(FIG. 8A) The diagram of polyQ tagged GFP and the plasmid map. Mainly, either 22 or 44 polyQ was in-frame fused with GFP in the pEGFP1 plasmid. (FIG. 8B) HEK 293 cells were transfected with pEGFPC1-Q44. Left panel, 24 hours after transfection, the GFP signals can be clearly observed using a fluorescence microscope. Right panel, aggregated GFP (arrow) appears in the cells 48 hours after transfection.

(FIG. 9A) The representation provides images of cells transfected with different poly Q constructs under different doses of HD 101 treatment. (FIG. 9B) After quantitation, the intensity of GFP was normalized with the intensity of DAPI, and was presented in the bar graph. The normalized intensity from cells with no drug treatment in each construct group was taken as 1 fold and the intensity of the drug treated samples were compared to the no drug treatment value and showed as fold change. Each bar contained the average data from 4 individual images.

DEFINITIONS

Figure 1:
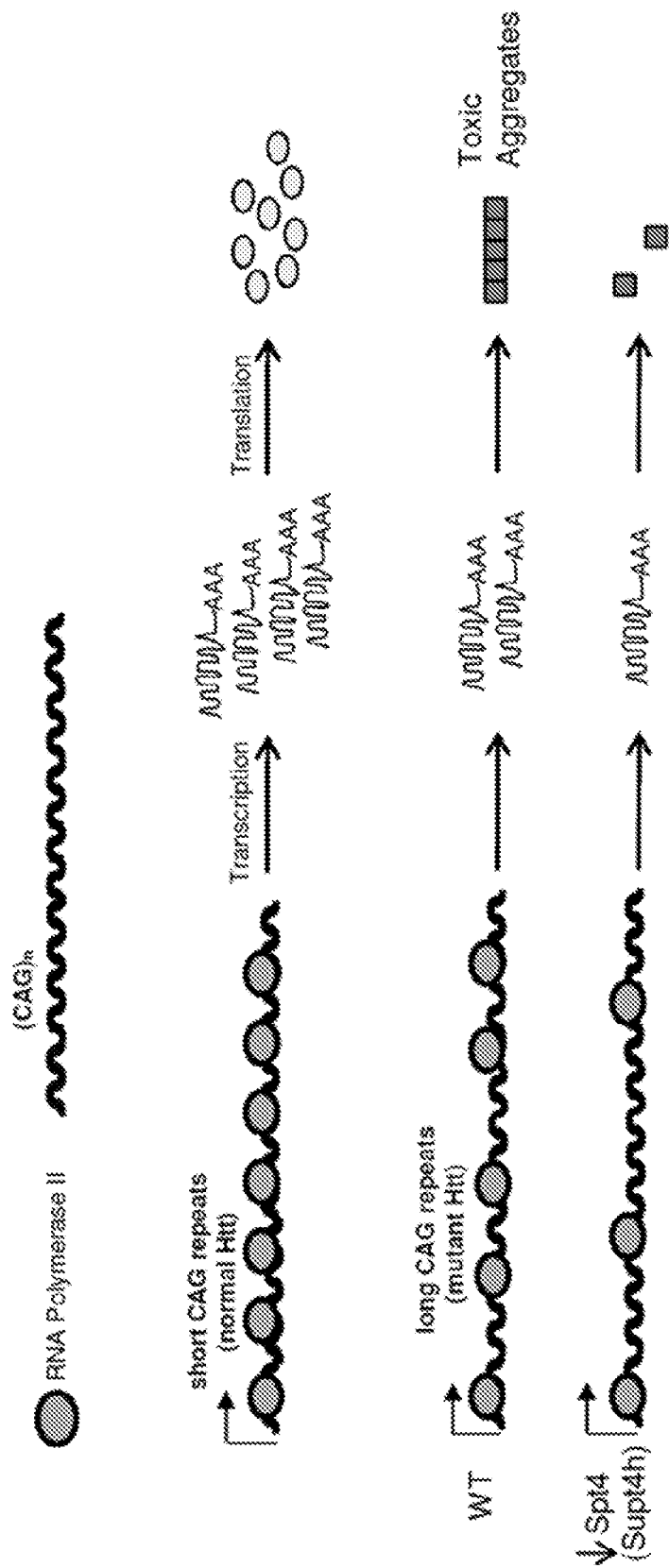
FIG. 1 depicts the effect and consequence of Spt4 (Supt4h) inhibition on expression of extended tri-nucleotide repeat (TNR) (e.g., CAG repeat) containing genes. When RNA polymerase II moves along a DNA template containing a short CAG repeat (indicated by the grey oval), transcript elongation by Spt4 may not be essential for production of the RNA and protein encoded by normal alleles of the gene. However, transcription elongation becomes less efficient and requires Spt4 when a long CAG stretch is present in the gene. In cells lacking normal Spt4 function, only genes containing extended stretches of CAG repeats and encoding expanded polyQ proteins are affected. Proteins containing expanded polyQ repeat (squares) aggregate (rectangle) in a concentration-dependent manner.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH$_2$—), sec-butyl (($CH_3$)($CH_3CH_2$)CH—), t-butyl (($CH_3)_3$C—), n-pentyl ($CH_3CH_2CH_2CH_2CH_2$—), and neopentyl (($CH_3)_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). In some cases, alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. In some cases, alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein. The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, $—NR^{80}R^{80}$ is meant to include $—NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified: $—R^{60}$, halo, $—O^-M^+$, $—OR^{70}$, $—SR^{70}$, $—S^-M^+$, $—NR^{80}R^{80}$, trihalomethyl, $—CF_3$, $—CN$, $—OCN$, $—SCN$, $—NO$, $—NO_2$, $—N_3$, $—SO_2R^{70}$, $—SO_3^-M^+$, $—SO_3R^{70}$, $—OSO_2R^{70}$, $—OSO_3^-M^+$, $—OSO_3R^{70}$, $—PO_3^{-2}(M^+)_2$, $—P(O)(OR^{70})O^-M^+$, $—P(O)(OR^{70})_2$, $—C(O)R^{70}$, $—C(S)R^{70}$, $—C(NR^{70})R^{70}$, $—CO_2^-M^+$, $—CO_2R^{70}$, $—C(S)OR^{70}$, $—C(O)NR^{80}R^{80}$, $—C(NR^{70})NR^{80}R^{80}$, $—OC(O)R^{70}$, $—OC(S)R^{70}$, $—OCO_2^-M^+$, $—OCO_2R^{70}$, $—OC(S)OR^{70}$, $—NR^{70}C(O)R^{70}$, $—NR^{70}C(S)R^{70}$, $—NR^{70}CO_2^-M^+$, $—NR^{70}CO_2R^{70}$, $—NR^{70}C(S)OR^{70}$, $—NR^{70}C(O)NR^{80}R^{80}$, $—NR^{70}C(NR^{70})R^{70}$ and $—NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $—O^-M^+$, $—OR^{70}$, $—SR^{70}$, or $—S^-M^+$.

In addition to the groups disclosed with respect to the individual terms herein, substituent groups for hydrogens on nitrogen atoms in "substituted" heteroalkyl and cycloheteroalkyl groups are, unless otherwise specified, $—R^{60}$, $—O^-M^+$, $—OR^{70}$, $—SR^{70}$, $—S^-M^+$, $—NR^{80}R^{80}$, trihalomethyl, $—CF_3$, $—CN$, $—NO$, $—NO_2$, $—S(O)_2R^{70}$, $—S(O)_2O^-M^+$, $—S(O)_2OR^{70}$, $—OS(O)_2R^{70}$, $—OS(O)_2O^-M^+$, $—OS(O)_2OR^{70}$, $—P(O)(O^-)_2(M^+)_2$, $—P(O)(OR^{70})O^-M^+$, $—P(O)(OR^{70})(OR^{70})$, $—C(O)R^{70}$, $—C(S)R^{70}$, $—C(NR^{70})R^{70}$, $—C(O)OR^{70}$, $—C(S)OR^{70}$, $—C(O)NR^{80}R^{80}$, $—C(NR^{70})NR^{80}R^{80}$, $—OC(O)R^{70}$, $—OC(S)R^{70}$, $—OC(O)OR^{70}$, $—OC(S)OR^{70}$, $—NR^{70}C(O)R^{70}$, $—NR^{70}C(S)R^{70}$, $—NR^{70}C(O)OR^{70}$, $—NR^{70}C(S)OR^{70}$, $—NR^{70}C(O)NR^{80}R^{80}$, $—NR^{70}C(NR^{70})R^{70}$ and $—NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

Other definitions of terms may appear throughout the specification.

DETAILED DESCRIPTION

As summarized above, aspects of the invention include methods of reducing the deleterious activity of a mutant extended nucleotide repeat (NR) containing target gene in a cell by contacting the cell with an effective amount of a nucleoside agent, as well as compositions used in such methods. The deleterious activity (e.g., toxicity and/or dysfunctionality of products encoded thereby) of a mutant extended NR containing target gene may be reduced in a variety of different ways, e.g., by reducing (and in some instances differentially, including selectively, reducing) the production or activity of toxic expression products (e.g., RNA or protein) encoded by the target gene. Kits and compositions for practicing the subject methods are also provided. Methods and compositions of the invention find use in a variety of different applications, including the prevention or treatment of disease conditions associated with the presence of genes containing mutant extended nucleotide repeats, e.g., mutant extended trinucleotide repeats, such as Huntington's Disease (HD).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Aspects of the invention include reducing the deleterious impact in a cell of a target gene that includes an extended nucleotide repeat (NR) by contacting the cell with an effective amount of a nucleoside agent. In other words, embodiments of the invention include methods of reducing an extended nucleotide repeat-containing target gene's harmful or injurious activity in a cell. As used herein, the term "deleterious impact" refers to a harmful or injurious activity associated with, or attributable to, a target gene and which may result in an undesirable effect on the cell. By "reducing deleterious impact" is meant that the level of a harmful or injurious activity, or an undesirable effect thereof, is reduced by a statistically significant amount, and in some instances by 2-fold or more, such as by 5-fold or more, by 10-fold or more, by 20-fold or more, by 50-fold or more, by 100-fold or more, or even more, as compared to a control, e.g., a cell not contacted with the nucleoside agent of interest. The deleterious impact or activity of the target gene that is reduced by the subject nucleoside agents may vary, and may include, but is not limited to, cell toxicity, reduction in cell viability, loss of cellular function, formation of protein aggregates, etc. The subject methods and nucleoside agents may reduce the deleterious impact or activity of the target gene in a cell, via a method as described by Cheng et al. "Selective reduction of the deleterious activity of extended tri-nucleotide repeat containing genes" WO 2012078906, the disclosure of which is herein incorporated by reference in its entirety.

In certain embodiments, the methods may reduce the deleterious impact of an extended NR containing target gene by selectively reducing the deleterious impact of the target gene. As the methods of these embodiments are methods of selectively reducing the deleterious impact, i.e., activity, of the target gene, they do so while retaining at least a statistically measurable amount of normal or wild-type, e.g., beneficial, activity of the target gene, by which is meant the activity of the gene as present in normal or wild-type cells, which are cells in which the target gene does not include mutant extended nucleotide repeats (e.g., trinucleotide repeats) that give rise to deleterious activity. Accordingly, in these embodiments the subject methods may maintain or restore a physiologically desirable activity of the target gene despite the selective reduction of the harmful activity of the target gene. In some instances of the method, the nucleoside agent modulates the activity of a protein encoded by the target gene. In some embodiments of the method, the expression of the protein from the target gene is selectively modulated relative to expression from a normal allele of the target gene (e.g., a normal allele of the target gene includes 8 to 25 CAG repeats). In certain cases, the activity of a normal allele of the target gene is maintained in the cell, e.g., has an activity that is within 20% (such as within 10%, within 5%, within 2% or within 1%) of the corresponding activity of a control cell not contacted with the nucleoside agent of interest.

In yet other embodiments, the methods may reduce the deleterious impact in a cell of an extended NR containing target gene by reducing the deleterious impact as well as any normal activity of the target gene. As the methods of these embodiments are methods of non-selectively reducing the deleterious impact, i.e., activity, of the target gene, they reduce the deleterious impact of the target gene while also reducing to some extent, if not completely, the normal or wild-type, e.g., beneficial, activity of the target gene, by which is meant the activity of the gene as present in normal or wild-type cells, which are cells in which the target gene does not include mutant extended nucleotide repeats (e.g., TNRs) that give rise to deleterious activity.

In some cases, the harmful or injurious activity is a dysfunction of a protein product encoded by the target gene, where the dysfunction refers to an undesirable activity (e.g., cell toxicity) of the protein product that is not present in a normal allele of the target gene. In some instances, a target gene that does not include mutant extended nucleotide repeats that give rise to deleterious activity is referred to as a normal allele of the target gene. The normal allele of the target gene may include a desirable number of nucleotide repeats (NRs). In certain instances where the NR is a TNR, the normal allele includes 25 or less tri-nucleotide repeats (TNRs), such as 20 or less or 10 or less TNRs. In certain cases, the normal allele of the target gene includes 8 to 25 TNRs. In some instances, the normal allele includes 8 to 25 CAG repeats.

In certain embodiments of the method, the deleterious impact of the target gene is toxicity of the protein and the nucleoside agent reduces the toxicity of the protein in the cell. In some instances, toxicity is a result of undesirable protein aggregation. As such, in some instances the subject methods result in a reduction in toxicity that is attributable to the target gene, where the magnitude of the toxicity reduction may vary, and in some instances is 2-fold or greater, such as by 5-fold or greater, by 10-fold or greater, by 20-fold or greater, by 50-fold or greater, by 100-fold or greater, or even greater. e.g., as compared to a suitable control, e.g., a cell not contacted with the nucleoside agent of interest. As described in greater detail below, toxicity may be reduced in a number of different ways that may depend on the particular target gene. In some instances, e.g., where the target gene includes an extended CAG repeat that results in the presence of extended polyQ domains in a product encoded by the target gene, toxicity reduction may be accompanied by a reduction in aggregation of the products encoded by the target gene. In some embodiments of the method, the protein forms aggregates in the cell and includes a polyglutamine stretch with 26 or more glutamine residues, such as 30 or more glutamine residues, 35 or more, 40 or more, 50 or more, or 60 or more glutamine residues.

In such instances, the magnitude of the reduction in aggregation may vary, and in some instances the magnitude of reduction is 2-fold or more, such as by 5-fold or more, by 10-fold or more, by 20-fold or more, by 50-fold or more, by 100-fold or more, or even more, e.g., as compared to a suitable control, e.g., a cell not contacted with the nucleoside agent of interest. Protein aggregation may be assayed using any convenient protocol, including but not limited to, the protocols described in Published United States Patent Application No. 20110130305; the disclosure of which protocols are herein incorporated by reference.

In certain embodiments, the deleterious impact or activity that is reduced by methods of the invention may be loss of function of a product encoded by the target gene. In certain of these embodiments, the wild-type or normal activity of the product encoded by the target gene is at least partially, if not completely, impaired because the target gene includes the extended trinucleotide repeat. In these instances, the loss of function is at least partially, if not completely, reversed by enhancing the desired function of the product of the target gene. The desired function of the encoded product may be enhanced by a statistically significant amount as compared to a suitable control, e.g., a cell not contacted with the nucleoside agent of interest, where the magnitude of the enhancement in desired activity may be 2-fold or higher, such as 5-fold or higher, including 10-fold or higher.

In certain embodiments, the nucleoside agents increase the viability of the cell, as compared to a suitable control and as determined by a cell viability assay, e.g., as determined by contacting the cell with a compound of the invention to a cell and determining the number of viable cells in culture using a homogeneous method, such as the CellTiter-Glo® Luminescent Cell Viability Assay.

The target gene is a gene that includes a mutant extended NR, such as a TNR, where the mutant extended nucleotide repeat domain is not present in normal versions of the gene. The term "gene" as used herein is a defined region or portion of a chromosome that encodes or enables production of a product and includes a promoter, introns, exons and enhancers. By mutant extended nucleotide repeat (NR) is meant a domain (i.e., region) of the gene that includes multiple adjacent repeats of units of 2 or more nucleotides, where a given repeating unit of nucleotides may vary in length, ranging in some instances from 2 to 10 nucleotides, such as 3 to 6 nucleotides, where examples of repeat unit lengths include units of 2 nucleotides (e.g., where the mutant extended nucleotide repeat is a dinucleotide repeat), 3 nucleotides (e.g., where the mutant extended nucleotide repeat is a trinucleotide repeat), 4 nucleotides (e.g., where the mutant extended nucleotide repeat is a tetranucleotide repeat), 5 nucleotides (e.g., where the mutant extended nucleotide repeat is a pentanucleotide repeat) or 6 nucleotides (e.g., where the mutant extended nucleotide repeat is a hexanucleotide repeat). Within a given domain, the domain may be homogeneous or heterogeneous with respect to the nature of the repeat units that make up the domain. For example, a given domain may be made up of a single type of repeat unit, i.e., al the repeat units of the domain share the same (i.e., identical) sequence of nucleotides, such that it is a homogenous mutant NR domain. Alternatively, a given domain may be made up of two or more different types of repeat units, i.e., repeat units that have differing sequences, such that it is a heterogeneous mutant NR domain. The mutant extended nucleotide repeat domain may be present in a coding or non-coding region of the target gene. In some instances, the extended nucleotide repeat domain is present in a coding region of the target gene. In some instances, the extended nucleotide repeat domain is present in a non-coding region of the target gene. The length and particular sequence of the mutant extended nucleotide repeat may vary.

In some instances, the mutant extended nucleotide repeat is a mutant extended trinucleotide repeat. By mutant extended trinucleotide repeat is meant a domain (i.e., region) of the gene that includes multiple adjacent repeats of the same three nucleotides, where the length and particular sequence of the mutant extended trinucleotide repeat may vary and the mutant extended trinucleotide repeat domain is not present in normal versions of the gene. The extended trinucleotide repeat domain may be present in a coding or non-coding region of the target gene. In some instances, the extended trinucleotide repeat domain is present in a coding region of the target gene. In some instances, the extended trinucleotide repeat domain is present in a non-coding region of the target gene. In embodiments, the mutant repeat domain is present in a non-coding region of the target gene, such as the CTG expansion located in the 3' untranslated region of the dystrophia myotonica-protein kinase gene, which leads to Myotonic dystrophy (DM). In some instances, the mutant repeat domain is present in a coding region of the target gene, such that in some instances its presence in the target gene results in a corresponding domain or region (e.g., polyQ domain) in a product encoded by the gene. In some instances of the method, the mutant extended TNR domain is a CTG repeat domain. In certain cases, the mutant extended trinucleotide repeat domain includes 26 or more CTG repeats (e.g., 30 or more, 35 or more, etc).

The mutant extended trinucleotide repeat may vary in terms of nucleotide composition and length. Specific trinucleotides of interest include, but are not limited to: CAG, CTG, CGG, GCC, GAA, and the like. In some instances, the mutant extended trinucleotide repeat domain is a CAG repeat domain. The particular length of the repeat domain (e.g., CAG repeat domain) may vary with the respect to the specific target gene so long as it results in deleterious activity, and in some instances is 25 repeats or longer, such as 26 repeats or longer, 30 repeats or longer, including 35 repeats or longer, 40 repeats or longer, 50 repeats or longer or even 60 repeats or longer. Specific target genes and expressed proteins of interest, diseases associated therewith and the specific length of repeat sequences of extended CAG repeats of interest, include (but are not limited to) those provided in Table 1, below.

TABLE 1

| Disease | | disease name/ protein product | Pathogenic repeat length |
|---|---|---|---|
| Spinocerebellar ataxia type 1 | SCA1 | SCA1/ataxin 1 | 40~82 |
| Spinocerebellar ataxia type 2 | SCA2 | SCA2/ataxin 2 | 32~200 |
| Spinocerebellar ataxia type 3 | SCA3(MJD) | SCA3/ataxin 3 | 61~84 |
| Spinocerebellar ataxia type 7 | SCA7 | SCA7/ataxin 7 | 37~306 |
| Spinocerebellar ataxia type 17 | SCA17 | SCA17/TBP | 47~63 |
| Dentatorubral pallidoluysian atrophy | DRPLA | DRPLA/atrophin 1 | 49~88 |
| Spinal and bular muscular atrophy | SBMA | Kennedy's disease/androgen receptor protein | 38~62 |
| Huntington's disease | HD | Huntington's Disease/huntingtin protein | 40~121 |

The pathogenic repeat lengths shown are approximate and represent the most common range of pathogenic repeat lengths. The lower of the two numbers shown for each pathogenic repeat length indicates the length at which pathogenic effects of the expansion begin to occur. Although both cellular copies of autosomal genes responsible for NR diseases may contain NR domains, commonly one copy of the targeted gene is mutated to have an expanded NR segment, whereas the other copy (i.e., allele) contains a unexpanded NR.

As summarized above, the deleterious activity (e.g., toxicity and/or dis-functionality of products encoded thereby) of a mutant extended NR containing target gene may be reduced by the nucleoside agent in a variety of different ways, e.g., by reducing (and in some instances selectively reducing) the production or activity of toxic expression products (e.g., RNA or protein) encoded by the target gene, as described in greater detail below.

In some embodiments of the method, the nucleoside agent modulates the activity of a protein encoded by the target gene. For example, with respect to polyQ repeats, in certain embodiments, the target gene is selected from genes that produce the following diseases: SCA1, SCA2, SCA3, SCA7, SCA17, DRPLA, Kennedy's Disease and Huntington's Disease. In certain instances, the targeted disease is SCA1. In certain instances, the target disease is SCA2. In certain instances, the target disease is SCA3. In certain instances, the target disease is SCA7. In certain instances, the target disease is SCA17. In certain instances, the target disease is DRPLA. In certain instances, the target disease is Kennedy's Disease. In certain instances, the target disease is Huntington's Disease. Genes and their encoded proteins that give rise to these diseases are listed in Table 1, above. Any protein that is encoded by the target gene may be modulated, include post-translationally modified proteins. The modulated protein may be any expressed product of the gene, or a post-transcriptionally modified version thereof. In some cases, the protein is a Htt protein. In certain cases, the protein is a mutant Htt protein. Any post-translational modifications of huntingtin (Htt) proteins of interest may be modulated. Post-translational modifications of proteins of interest may regulate protein stability, localization, function, and their interactions with other molecules. Post-translational modifications may occur as chemical modifications at amino acid residues, including SUMOylation, phosphorylation, palmitoylation, acetylation, etc. Post-translational modifications may include enzymatic cleavage. Post-translational modifications may be involved in the regulation and control of a variety of cellular processes, such as Htt metabolism, protein-protein interactions and cellular toxicity.

In some instances, the agent modulates the functionality, e.g., binding properties, activity, etc., of the protein following expression, such that the agent is one that changes the functionality of the protein encoded by the target gene following expression of the protein from the target gene. In some cases, the agent may be one that selectively reduces the deleterious functionality, e.g., aggregation, of the encoded protein, but retains or enhances, at least to a detectable level, the beneficial activity of the encoded protein. In certain embodiments, such agents are not inhibitors of aggregation of the protein, but instead selectively reduce the deleterious activity or functionality of the protein via another mechanism, e.g., by reducing the amount of the protein in the cell that is available for aggregation, by reducing production of a protein that is detrimental to cells independently of its propensity to aggregate, etc.

In some embodiments, the nucleoside agent modulates expression of the RNA and/or protein from the gene, such that it changes the expression of the RNA or protein from the target gene in some manner. In certain embodiments of the method, the nucleoside agent modulates expression of the protein from the target gene. In certain cases of the method, the nucleoside agent differentially, and in some instances selectively, reduces transcription of the target gene to reduce toxicity in the cell of a protein encoded by the target gene. Any convenient assays may be used to determine a reduction in transcription in a cell using the subject nucleoside agents relative to a control, e.g., a cell not contacted with the nucleoside agent of interest, where the magnitude of transcription reduction may be 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more. In some instances of the method, the nucleoside agent differentially, and in some instances selectively, reduces transcription of the target gene to enhance functionality of the protein in the cell. By enhance functionality is meant that a natural, desirable function or activity of a protein encoded by the target gene is increased relative to a control, e.g., a cell not contacted with the nucleoside agent of interest, by 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more. Any convenient assays may be utilized to determine the level of function or activity of a protein of interest. By differentially reducing transcription of the target gene is meant that transcription of the target gene is reduced to an extent that is greater than any reduction of the non-target, e.g., corresponding wild-type, gene. The magnitude of any different in transcription resulting from administration of the agent may vary, where in some instances the magnitude of reduction of target gene transcription relative to corresponding non-target gene transcription is 2-fold or more, by 5-fold or more, by 10-fold or more, by 20-fold or more, by 50-fold or more, by 100-fold or more, or even more. In some instances, while transcription of the target gene is reduced, administration of the agent results in substantially little, if any, transcription reduction of the corresponding non-target gene. In such instances, administration of the agent may be viewed as selectively reducing transcription of the target gene.

In some cases, the nucleoside agent may change expression of a gene product, e.g., an RNA or protein. In certain embodiments of the method, the nucleoside agent reduces the deleterious impact by modulating functionality, e.g., changing binding interactions, of a SPT4 protein in the cell. The term SPT4 protein is used herein to collectively refer to not only yeast Spt4 proteins, but also mammalian homologs thereof, e.g., human SUPT4H; murine Supt4h, etc. As such, SPT4 proteins of interest whose activity may be modulated by the selective SPT4 modulatory agents include, but are not limited to: *S. cerevisiae* Spt4; human SUPT4H and murine Supt4h. Nucleoside agents of the invention may be referred to as SPT4 modulatory agents. SPT4 modulatory agents are agents that change the SPT4 activity in a cell, e.g., decrease SPT4 activity in a cell. The agent may be a selective SPT4 modulatory agent. In some instances, the target SPT4 activity that is modulated, e.g., decreased, by the active agent is a transcription activity, and specifically an activity that facilitates RNA polymerase II processivity through long trinucleotide repeat domains, e.g., long CAG repeat domains. The target SPT4 activity that is modulated by such agents is an activity arising from an SPT4 protein.

Where the nucleoside agent employed in methods of the invention is an SPT4 modulatory agent, the modulatory agent that is employed may be any convenient nucleoside agent that, upon introduction into a cell, changes the SPT4 functionality in the cell, and at least differentially reduces the extended trinucleotide repeat mediated SPT4 transcription activity in the subject. The SPT4 modulatory agent may modulate functionality in a variety of ways, e.g., by inhibiting binding of an SPT4 protein to another protein, e.g., a protein interacting with SPT4 (e.g., an SPT5 protein, such as Spt5 or SUPT5H), etc. In some instances, the nucleoside agent diminishes interaction of the SPT4 protein and a second protein. In certain instances, the second protein is a SPT5 protein. The term SPT5 protein is used herein to collectively refer to not only yeast Spt5 proteins, but also mammalian homologs thereof, e.g., human SUPT5H; murine Supt5h, etc. In certain embodiments of the method, the nucleoside agent diminishes interaction between Supt4h and Supt5h. Human Supt4h may form a complex with Supt5h as may its yeast ortholog to regulate transcription elongation (Guo et al., "Core structure of the yeast spt4-spt5 complex: a conserved module for regulation of transcription elongation," Structure (2008) 16: 1649-1658; Hatzog et al., "Evidence that Spt4, Spt5, and Spt6 control transcription elongation by RNA polymerase II in *Saccharomyces cerevisiae*," Genes Dev. (1998) 23:357-369; Wada et al., "DSIF, a novel transcription elongation factor that regulates RNA polymerase II processivity, is composed of human Spt4 and Spt5 homologs," Genes Dev (1998) 12: 343-356; Wenzel et al., "Crystal structure of the human transcription elongation factor DSIF hSpt4 subunit in complex with the hSpt5 dimerization interface," Biochem J (2009) 425: 373-380). In certain embodiments of the method, the nucleoside agent diminishes interaction between Supt5h and RNA polymerase II. For example, a nucleoside active agent may interfere with binding of Supt 5h to RNA polymerase II, and its effects on the interaction between Supt4h and Supt5h may be indirect.

Also provided are methods of diminishing interaction of a SPT4 protein (e.g., as described herein) and a second protein in a sample by contacting the sample with an effective amount of a nucleoside agent that differentially, if not selectively, diminishes the interaction of the SPT4 protein and the second protein. In certain instances, the second protein is a SPT5 protein (e.g., as described herein). By "diminishes interaction" is meant that the extent of binding of the SPT4 protein to the second protein (e.g., a fraction of bound SPT4 as compared to total SPT4) is reduced by 10% or more, such as 20% or more, 30% or more, 50% or more, 100% or more, such as by 2-fold or more, by 5-fold or more, by 10-fold or more, by 20-fold or more, by 50-fold or more, by 100-fold or more, or even more, e.g., as compared to a suitable control, e.g., a cell not contacted with the nucleoside agent of interest. Any convenient methods may be utilized to determine extent of binding of the SPT4 protein to the second protein. In certain embodiments of the method, the nucleoside agent diminishes interaction between Supt4h and Supt5h. The nucleoside agent may specifically bind to the SPT4 protein and disrupt the interaction of the SPT4 protein with the SPT5 protein. In some instances, the nucleoside agent specifically binds to the SPT5 protein and disrupts the interaction between the SPT4 and SPT5 protein.

In some instances, an effective amount of a nucleoside agent is an interaction diminishing amount, i.e., an amount of the nucleoside agent that inhibits the formation of a SPT4 complex (e.g., a SPT4/SPT5 complex) by 20% or more, such as 30% or more, 40% or more, 50% or more, 60% or more, 70% or more, 80% or more, or even 90% or more, as compared to SPT4 complex formation in the absence of the nucleoside agent. Any convenient methods of assaying inhibition of complex formation or competitive inhibition may be utilized, such as those methods described by Cheng et al. "Selective reduction of the deleterious activity of extended tri-nucleotide repeat containing genes" WO 2012078906, the disclosure of which assay methods are herein incorporated by reference.

Any convenient cells may be targeted for use in the subject methods. In some instances, the types of cells in which the nucleoside agent exhibit activity are ones that include a target gene containing a mutant extended trinucleotide repeat. In some embodiments of the method, the cell is an animal cell or a yeast cell. In certain instances, the cell is a mammalian cell.

In practicing methods according to embodiments of the invention, an effective amount of the nucleoside agent, e.g., SPT4 modulatory agent, is provided in the target cell or cells. In some instances, the effective amount of the modulatory agent is provided in the cell by contacting the cell with the modulatory agent. Contact of the cell with the modulatory agent may occur using any convenient protocol. The protocol may provide for in vitro or in vivo contact of the modulatory agent with the target cell, depending on the location of the target cell. In some instances, the cell is in vitro. In certain instances, the cell is in vivo. Contact may or may not include entry of the agent into the cell. For example, where the target cell is an isolated cell and the modulatory agent is an agent that modulates expression of SPT4, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the nucleoside agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are in some cases returned to a living body.

In certain embodiments, the method is an in vivo method that includes: administering to a subject in need thereof an effective amount of a nucleoside agent that selectively reduces the deleterious impact of the target gene to modify progression of a disease arising from the target gene in the subject. The term "treating" or "treatment" as used herein means the treating or treatment of a disease or medical condition in a patient, such as a mammal (such as a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient. As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human.

In some instances, the method delays occurrence of a symptom associated with the disease. In certain instances, the method reduces the magnitude of a symptom associated with the disease. Disease conditions of interest include those associated with the deleterious activity of genes containing mutant extended trinucleotide repeat domains. The term "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition). Specific disease conditions in which the methods and compositions of the invention find use include, but are not limited to, those listed in the Introduction section above, and include polyQ disease conditions, such as Spinocerebellar ataxia type 1, Spinocerebellar ataxia type 2, Spinocerebellar ataxia type 3, Spinocerebellar ataxia type 7, Spinocerebellar ataxia type 17, Dentatorubral pallidoluysian atrophy, spinobulbar muscular atrophy, and Huntington's Disease; other trinucleotide repeat diseases, e.g., Fragile X syndrome, Fragile XE MR, Fragile X tremor/ataxia syndrome (FXTAS), myotonic dystrophy, Friedreich's ataxia, spinocerebellar ataxia 8 (SCA8), and spinocerebellar ataxia 12 (SCA12); polyalanine expansion disorders, e.g., myotonic dystrophy type 2, spinocerebellar ataxia 10, spinocerebellar ataxia 31, progressive myoclonic epilepsy; hexanucleotide repeat disease conditions, e.g., autosomal-dominant frontotemporal dementia (FTD) and amyotrophic lateral sclerosis (ALS); and the like.

The term "surrogate marker" is employed in its conventional sense to refer to a measure of the effects of specific disease treatment or predict outcomes in a clinical trial. Surrogate markers can be defined as a laboratory measurement or a physical sign that is used in therapeutic trials as a substitute for a clinically meaningful endpoint. Reliable surrogates, rigorously validated in phase III clinical trials, can forecast the long term effect of the therapy based on how the patient feels, functions, or survives (Katz, "Biomarkers and Surrogate Markers: an FDA Perspective," NeuroRx (2004) 1: 189-95). These markers may also be used to compare drug efficacy between trials and may even become the basis for which new drugs gain regulatory approval for marketing (Twaddell, "Surrogate outcome markers in research and clinical practice," Australian Prescriber (2009) 32: 47-50). Because their use can reduce the size, duration, and cost of large studies or clinical trials, these markers are especially valuable if the predicted drug effect prevents death or promotes other critically important outcomes. For some progressive diseases, surrogate markers may be able to determine the disease stage (Weston, "The use of surrogate end points in cardiovascular disease and diabetes," The British Journal of Cardiology (2008) 15: S6-S7). Depending on the specific disease condition, surrogate markers may vary widely. Embodiments of the invention therefor include administering an active agent, e.g., as described herein, to modulate, e.g., improve, one or more surrogate markers of the disease condition.

For example, where the target disease condition being treated is Huntington's Disease, a variety of different surrogate markers may be employed to monitor the disease and the effect of therapy thereon. A protocol considered a standard method of assessing the clinical features and course of Huntington's Disease is the Unified Huntington's Disease Rating Scale (UHDRS). The method evaluates Huntington's Disease patients in four areas: motor function, cognitive function, behavioral abnormalities and functional capacity. The motor section provides a scale ranging from 0 to 4 for rating oculomotor function, dysarthria, chorea, dystonia, gait, and postural stability. A higher total score indicates more severe motor impairment. Next, a patient's cognitive function is assessed with three tests, which are a phonetic verbal fluency test, the Symbol Digit Modalities Test, and the Stroop Interference Test. Here, higher raw scores from each test indicate better cognitive performance. The behavioral portion of the protocol measures the frequency and severity of abnormalities in mood, behavior, and psychosis with a scale ranging from 0 to 4, with 0 representing an absence of a behavior and 4 representing a severe manifestation of a behavior. The total behavior score is the sum of all responses, and a higher score indicates a greater severity of behavioral symptoms. The behavioral section also prompts the evaluator to determine if the patient shows evidence of confusion, dementia, or depression. Incorporating radiographic measures of disease progression, the functional assessments include the total functional capacity score, the independence scale, and a checklist of tasks. The total functional capacity score derives from a scale ranging from 0 to 2 or 3, with 0 representing an inability to operate normally and 2 or 3 representing normal functional capacity. The independence scale ranges from 0 to 100, with each increment of 10 representing a decreased need for special care, assistance, and supervision. The checklist of questions regarding the patient's ability to carry out a task is summed by giving a score of 1 to all "yes" replies. Higher scores represent better patient functioning than lower scores (Kieburtz, et al., "Unified Huntington's Disease Rating Scale: Reliability and Consistency," Movement Disorders (1996) 11: 136-42). Practice of embodiments of the methods results in improvement in one or more, including all of the UHDRS parameters, where the improvement in some instances is 5% or greater, such as 10% or greater, and in some instances may be 100%, or even greater.

Results from other behavioral and task completion tests may serve as surrogate markers for Huntington's Disease in embodiments of the invention. The Reading the Mind in the Eyes Test (RMET), for instance, is a surrogate measure of amygdala function that is clinically useful across all disease stages in Huntington's. It is based on an individual's ability to understand the presence of beliefs, feelings, intentions and interest in other people that can differ from their own or from reality. Patients are shown a picture of the eyes and are asked to determine which of four emotional/mental state words positioned around the picture best captures the thoughts or feelings portrayed in the eyes. Performance on this test, determined by the total number of correct responses, was found to correlate negatively with proximity to disease onset and became progressively worse with each stage of disease (Mason, et al., "The role of the amygdala during emotional processing in Huntington's disease: From pre-manifest to late stage disease," Neuropsychologia (2015) 70: 80-9). Patient speech patterns have also been analyzed for use as a marker of Huntington's Disease. Patients can be asked to read a passage or produce a monologue. Research has shown patients carrying the mutant Huntingtin (Htt) gene present with slower rates of speech, take longer to say words and produce greater silences between and within words compared to healthy individuals (Vogel, et al., "Speech acoustic markers of early stage and prodromal Huntington's disease: a marker of disease onset?," Neuropsychologia (2012) 50: 3273-8). Other markers include dual-task performance tests, where Huntington's Disease patients are slower and less accurate at performing simple tasks alone or together, and eye movements, which can provide information about disease severity and progression (Vaportzis, et al., "Effects of task difficulty during dual-task circle tracing in Huntington's disease," Journal of Neurology (2015) 262: 268-76), (Anderson and MacAskill, "Eye movements in patients with neurodegenerative disorders," Nature Reviews. Neurology (2013) 9: 74-85). Other markers include, but are not limited to, the Choice Reaction Task to evaluate subtle motor dysfunction, the Hopkins Verbal Learning Test to evaluate episodic memory, a computerized Mental Rotation Task to assess visuospatial processing, and a set-shifting task (Rosas, et al., "PRECREST: a phase II prevention and biomarker trial of creatine in at-risk Huntington disease," Neurology (2014) 82: 850-7), (Beste, et al., "A novel cognitive-neurophysiological state biomarker in premanifest Huntington's disease validated on longitudinal data," Sci. Rep. (2013) 3:1-8). Practice of embodiments of the methods results in improvement in the parameters being measured in the particular test that is employed, where the improvement in some instances is 5% or greater, such as 10% or greater, and in some instances may be 100%, or even greater.

In other instances, samples taken from the blood, tissues and body fluids of Huntington's Disease patients are analyzed for surrogate markers. These markers may vary, where examples of such markers include analytes found in serum or physical measurements, such as pH or blood volume. The concentration, levels, or quantitative measurements of such markers in body fluids and tissues are often found to correspond with the emergence of Huntington's Disease symptoms. For example, increased serum levels of oxysterols such as free 24S-hydroxycholesterol and the 24S-hydroxycholesterol/total cholesterol ratio were associated with greater risk of impairment on tasks that assessed psychomotor speed and executive functioning. Meanwhile, higher levels of free 27-hydroxycholesterol and the 27-hydroxycholesterol/total cholesterol ratio were associated with greater risk of delayed memory impairment (Bandaru and Haughey, "Quantitative detection of free 24S-hydroxycholesterol, and 27-hydroxycholesterol from human serum," BMC Neuroscience (2014) 15: 137). Another example of a marker found in body fluid is cortisol, of which higher concentrations in saliva was strongly associated with reduced information encoding and memory retrieval and increased motor sign severity in pre- or early-Huntington's Disease patients (Shirbin, et al., "The relationship between cortisol and verbal memory in the early stages of Huntington's Disease," Journal of Neurology (2013) 260: 891-902). Demonstrating that physical measures may have use as surrogate markers, studies found an increase in neuronal pH and cerebral blood volume in prodromal or early-Huntington's Disease patients (Hua, et al., "Elevated arteriolar cerebral blood volume in prodromal Huntington's Disease," Movement Disorders (2014) 29: 396-401), (Chaumeil, et al., "pH as a biomarker of neurodegeneration in Huntington's disease: a translational rodent-human MRS study," Journal of Cerebral Blood Flow (2012) 32: 771-9). Yet another instance of a molecular surrogate is transcript expression, specifically the decrease after treatment in expression of genes that were initially expressed at higher levels in Huntington's Disease subjects compared to healthy individuals (Borovecki, et al, "Genome-wide expression profiling of human blood reveals biomarkers for Huntington's Disease," PNAS (2005) 102: 11023-028). Other surrogate markers in body fluids include, but are not limited to: C-reactive proteins, myeloperoxidase (MPO)/white blood cell (WBC) ratio, interleukin-6 (IL-6), thioredoxin reductase-1 (TrRd-1), thioredoxin-1 (Trx-1), and muscle adenosine triphosphate (Sánchez-López, et al., "Oxidative stress and inflammation biomarkers in the blood of patients with Huntington's disease," Neurological Research (2012) 34: 721-4), (Lodi, et al., "Abnormal in vivo skeletal muscle energy metabolism in Huntington's disease and dentatorubropallidoluysian atrophy," Annals of Neurology (2000) 48: 72-6). Practice of embodiments of the methods results in improvement in the marker(s) being measured in the particular test that is employed, where the improvement in some instances is 5% or greater, such as 10% or greater, and in some instances may be 100%, or even greater.

Additionally, surrogate markers for Huntington's Disease may be imaging markers, e.g., markers obtained by neuroimaging and magnetic resonance imaging (MRI). Imagining is employed to provide information about volume, levels of atrophy, and activity in white and grey matter across regions of the brain. As described by van den Bogaard et al., "MRI biomarkers in Huntington's Disease," Frontiers in Bioscience (2012) 4: 1910-25. Common MRI methods include structural MRI, Diffusion Tensor Imaging, Magnetization Transfer Imaging, Magnetic Resonance Spectroscopy, and Functional MRI. Structural or volumetric MRI can reveal regional, progressive thinning of the cortical ribbon and grey and white matter reductions. Structural MRI scans can also detect the amount and rates of atrophy in brain regions, especially the caudate nucleus, globus pallidus, and putamen, which appears to occur in a pre- or early-disease state. Various semi- to fully-automate techniques such as Voxel Based Morphometry (VBM), Boundary Shift Integral (BSI) and FMRIB's Integrated Registration and Segmentation Technique (FIRST) have been described (van den Bogaard, et al., "MRI biomarkers in Huntington's Disease," Frontiers in Bioscience (2012) 4: 1910-25). With Diffusion Tensor Imaging (DTI), the integrity of tissue matter is evaluated based upon the diffusion properties of protons in the intra- and extracellular space. Disturbances in fractional anisotrophy (FA), Apparent Diffusion Coefficient (ADC), mean diffusivity (MD) and total diffusivity (TraceD) in white and great matter are measured during a DTI scan. An FA value close to 0 is representative of equal diffusion in all directions. In contrast, an FA value close to or equal to 1 represents highly directional diffusion. High MD-values represent unrestricted diffusion and low MD-values suggest restricted diffusion. An increase in MD and FA values in several regions of the brain collectively demonstrated selective degeneration of connections in subcortical grey and white matter, which was likely due to the death of the striatal medium-size spiny neurons in Huntington's Disease (Douaud, et al., "In vivo evidence for the selective subcortical degeneration in Huntington's disease," NeuroImage (2009) 46: 958-66), (van den Bogaard, et al., "MRI biomarkers in Huntington's Disease," Frontiers in Bioscience (2012) 4: 1910-25). Another technique, Magnetization Transfer Imaging (MTI), provides a way to examine tissue structure. The technique relies on the interaction between protons in free fluid and protons bound to macromolecules. The magnetization saturation and relaxation within macromolecules affect the observable signal. The Magnetization Transfer Ratio (MTR), representing the percentage of variation in the MR signal between the saturated and unsaturated acquisitions, is a measure used in clinical studies. Two main outcome measures, the mean MTR and the MTR peak height from histogram analysis, are reported. In a study of Huntington's Disease carriers, the MTR was significantly decreased in all subcortical structures except the putamen, revealing degeneration of the subcortical and cortical grey matter (Ginestroni, et al., "Magnetization transfer MR imaging demonstrates degeneration of the subcortical and cortical gray matter in Huntington's Disease," American Journal of Neuroradiology (2010) 31: 1807-12), (van den Bogaard, et al., "MRI biomarkers in Huntington's Disease," Frontiers in Bioscience (2012) 4: 1910-25). Yet another technique is Magnetic Resonance Spectroscopy (MRS). MRS uses hydrogen protons to measure metabolite concentrations. Unlike previous techniques, MRS gives information about changes in physiological processes. The most common metabolites examined are: N-acetylaspertate, a marker for neuronal and axonal integrity, Creatine, a marker for brain energy metabolism, Choline, a marker reflecting membrane turnover, Myo-inositol, a marker of osmolytes and astrocytes, Lactate, a marker of interruptions of oxidative processes and the beginning of anaerobic glycolysis, and glutamate, a neurotransmitter. Decreased levels of creatine and N-acetylaspertate and increased levels of lactate across different brain regions have been reported in premanifest Huntington's disease studies (van den Bogaard, et al., "MRI biomarkers in Huntington's Disease," Frontiers in Bioscience (2012) 4: 1910-25). Finally, functional MRI (fMRI) uses the blood-oxygen-level-dependent (BOLD) signal to discriminate brain regions with altered activation. Activation of a brain region requires an increase in energy and, consequently, blood demand, measured with fMRI. Different functional tasks such as a clock reading task, verbal working memory task, Simon task, or a porteus maze task can be employed during fMRI scanning. Abnormal connectivity or activation patterns are associated with premanifest and manifest Huntington's Disease. For instance, premanifest Huntington's Disease patients often show increased activation of several regions while there generally is a reduction of activation in premanifest gene carriers "close to onset" (van den Bogaard, et al., "MRI biomarkers in Huntington's Disease," Frontiers in Bioscience (2012) 4: 1910-25). According to Van den Bogaard, volumetric measures and white matter diffusion tensor imaging integrity measures are the best techniques for assessing the pre-manifest stage of Huntington's disease. For early manifest Huntington's Disease, Magnetic Transfer Imaging and measurements of whole brain atrophy are more appropriate (van den Bogaard, et al., "MRI biomarkers in Huntington's Disease," Frontiers in Bioscience (2012) 4: 1910-25). Practice of embodiments of the methods results in improvement in the parameters being measured in the particular imaging test that is employed, where the improvement in some instances is 5% or greater, such as 10% or greater, and in some instances may be 100%, or even greater.

Separate from MRI scans, Positron Emission Tomography (PET) scans have also been employed to measure cerebral metabolic activity in premanifest Huntington's Disease patients at baseline and later in subsequent years. Metabolic brain network analysis has been increasingly used to measure the expression of characteristic spatial covariance patterns in patients experiencing neurodegeneration. Measured with [$^{18}$F]-fluorodeoxyglucose scans, metabolic network activity proved sensitive to disease progression as demonstrated by its rapid rate of progression and high expression during the clinical onset of Huntington's Disease, also called phenoconversion. Abnormal elevations in baseline metabolic activity above a certain threshold indicated a high likelihood of phenoconversion in the coming years (Tang, et al., "Metabolic network as a progression biomarker of premanifest Huntington's disease," The Journal of Clinical Investigation (2013) 123: 4076-88). A decrease in cortical glucose metabolism in the bilateral frontal, temporal and parietal cortices is also suggested as a predictor for identifying a more rapid form of disease progression in early stage Huntington's Disease patients (Shin, et al., "Decreased Metabolism in the Cerebral Cortex in Early-Stage Huntington's Disease: A Possible Biomarker of Disease Progression?," Journal of Clinical Neurology (2013) 9: 21-5). Practice of embodiments of the methods results in improvement in the parameters being measured in the particular imaging test that is employed, where the improvement in some instances is 5% or greater, such as 10% or greater, and in some instances may be 100%, or even greater.

Beyond body fluid based markers and imaging markers, surrogate markers for Huntington's Disease include a variety of dietary, mineral accumulation, and inclusion detection measures. One study assessed the influence of adherence to a Mediterranean diet on phenoconversion and found some correlation between high consumption of dairy products with an increased risk of higher urate levels, associated with faster progression in manifest Huntington's disease (Marder, et al., "Relationship of Mediterranean diet and caloric intake to phenoconversion in Huntington's Disease," JAMA Neurology (2013) 70: 1382-8). In a separate study, iron accumulation was detected in the globus pallidus in both pre-Huntington's and symptomatic patients (Sanchez-Castañeda, et al., "Seeking Huntington's disease biomarkers by multimodal, cross-sectional basal ganglia imaging," Human Brain Mapping (2013) 34: 1625-35). Another surrogate marker involves evaluation of intra-neuronal aggregates of huntingtin protein and protein fragments containing expanded polyglutamine repeats (Sieradzan, et al., "The selective vulnerability of nerve cells in Huntington's disease," Neuropathology and Applied Neurobiology (2001) 27: 1-21), (Huang, et al., "Inducing huntingtin inclusion formation in primary neuronal cell culture and in vivo by high-capacity adenoviral vectors expressing truncated and full-length huntingtin with polyglutamine expansion," The Journal of Gene Medicine (2008) 10: 269-79). In mice, gait analysis, immunostaining with the antibody EM48, and filter trap assays were employed together to show that early nuclear accumulation of mutant huntingtin protein or protein fragments in striatal neurons correlates with later striatal degeneration and motor deficits. Striatal phenotypes, therefore, specifically demonstrate that the disease progression is hastened by a mutant huntingtin protein fragment and may serve as surrogate markers predicting onset of Huntington's Disease (Wheeler, et al., "Early phenotypes that presage late-onset neurodegenerative disease allow testing of modifiers in Hdh CAG knock-in mice," Human Molecular Genetics (2002) 11: 633-40). Immunostaining patterns of antibodies such as the monoclonal antibody 1C2, capable of detecting long stretches of glutamine residues, also have the potential to provide diagnostic assistance in the postmortem central nervous system analysis of Huntington's Disease (Herndon, et al., "Neuroanatomical Profile of Polyglutamine Immunoreactivity in Huntington Disease Brains," Journal of neuropathology and experimental neurology (2009) 68: 250-61). Practice of embodiments of the methods results in improvement in the parameters being measured in the particular test that is employed, where the improvement in some instances is 5% or greater, such as 10% or greater, and in some instances may be 100%, or even greater.

In the subject methods, the nucleoside agent may be administered to the targeted cells using any convenient administration protocol capable of resulting in the desired activity. Thus, the agent can be incorporated into a variety of formulations, e.g., pharmaceutically acceptable vehicles, for therapeutic administration.

Nucleoside Agents

Aspects of the invention include nucleoside agents that reduce the deleterious activity of a mutant extended trinucleotide repeat containing target gene in a cell. A nucleoside agent is a compound that includes a sugar moiety linked to a heterocyclic base moiety. The sugar moiety may be linked to the heterocyclic base moiety via a glycosidic linkage. In some cases, the glycosidic linkage is an α-glycosidic bond. In certain cases, the glycosidic linkage is a β-glycosidic bond.

Sugar moieties of interest include, but are not limited to, not only conventional ribose and deoxyribose sugars and conventional stereoisomers, but other sugars as well, including L enantiomers and alpha anomers, and derivatives and analogs thereof, such as, D-ribopyranose and D-ribofuranose, deoxy derivatives thereof, phosphorylated derivatives thereof, acylated derivatives thereof, fluorinated derivatives thereof and analogues thereof. As used herein, the term "nucleoside agent" is meant to include both phosphorus containing agents (e.g., nucleoside agents that include O-phosphate substituted sugar moieties) and agents that lack a phosphorus moiety. Nucleosides agent of interest may include any convenient modifications to the sugar moiety, e.g., modifications where a naturally occurring hydroxyl group is replaced with a halogen atom or an aliphatic group, or is functionalized as an ether, an amine, or the like. "Analog" refer to molecules having structural features that are recognized in the literature as being mimetics, derivatives, having analogous structures, or other like terms, and include, for example, non-natural (not usually occurring in nature) nucleosides, unnatural nucleoside mimetics such as 2'-modified nucleosides including but not limited to 2'-fluoro, 2'-O-alkyl, O-alkylamino, O-alkylalkoxy, protected O-alkylamino, O-alkylaminoalkyl, O-alkyl imidazole, and polyethers of the formula (O-alkyl)$_m$ such as linear and cyclic polyethylene glycols (PEGs), and (PEG)-containing groups, and groups such as those found in locked nucleic acids (LNA), peptide nucleic acids (PNA), oligomeric nucleoside phosphonates, and any polynucleotide that has added substituent groups, such as protecting groups or linking groups. "Deoxy" substituents that find use in sugar moieties include hydrogen (i.e. deoxyribose sugars); halo (e.g., fluoro); protected amino (e.g. $NH_2$; alkylamino, dialkylamino, heterocyclyl, arylamino, diaryl amino, heteroaryl amino, diheteroaryl amino, or amino acid in which all amino are protected); fully protected polyamino (e.g., $NH(CH_2CH_2NH)_nCH_2CH_2$-AMINE, where AMINE may be $NH_2$; alkylamino, dialkylamino, heterocyclyl, arylamino, diaryl amino, heteroaryl amino, or diheteroaryl amino and all amino groups are protected), —NHC(O)R(R=alkyl, cycloalkyl, aryl, aralkyl, heteroaryl or sugar), cyano; alkylthio-alkyl; thioalkoxy; and alkyl, cycloalkyl, aryl, alkenyl and alkynyl, which may be optionally substituted with e.g., a protected amino functionality. Preferred substitutents are 2'-methoxyethyl, 2'-$OCH_3$, 2'-O-allyl, 2'-C-allyl, and 2'-fluoro. A "ribonucleoside agent" is a nucleoside agent that contains a ribose sugar moiety, including modified ribose sugar moieties.

The term "heterocyclic base moiety" is intended to include those moieties that contain not only the known purine and pyrimidine bases, e.g. adenine (A), thymine (T), cytosine (C), guanine (G), or uracil (U), but also other heterocyclic bases or nucleobases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, substituted thiourea or the like. The purine or pyrimidine base may also be an analog of the foregoing; suitable analogs will be known to those skilled in the art and are described in the pertinent texts and literature. Analogs of interest include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

Any convenient nucleoside agents may find use in the subject methods and compositions. Such nucleoside agents may be assessed, among other ways, by employing the screening methods described by Cheng et al. "Selective reduction of the deleterious activity of extended tri-nucleotide repeat containing genes" WO 2012078906, the disclosure of which screening method is herein incorporated by reference. Nucleoside agents of interest include, but are not limited to, 5-fluorouracil (5-FU), 5-FU prodrugs including tegafur and 5'-deoxyfluorouridine, fluorouridine, 2'-deoxyfluorouridine, prodrug derivatives of fluorouridine or 2'-deoxyfluorouridine, fluorocytosine, trifluoro-methyl-2'-deoxyuridine, arabinosyl cytosine, prodrugs of arabinosyl cytosine, cyclocytidine, 5-aza-2'-deoxycytidine, arabinosyl 5-azacytosine, 6-azacytidine, N-phosphonoacetyl-L-aspartic acid (PALA), pyrazofurin, 6-azauridine, azaribine, thymidine, 3-deazauridine, triacetyluridine, ethoxycarbonyluridine, triacetylcytidine, cyclocytidine, 5-aza-2'-deoxycytidine, arabinosyl 5-azacytosine, 6-azacytidine, benzylacyclouridine, benzyloxybenzylacyclouridine, aminomethyl-benzylacyclouridine, aminomethyl-benzyloxybenzylacyclouridine-, hydroxymethyl-benzylacyclouridine, hydroxymethyl-benzyloxybenzylacyclouridine, 2,2'-anhydro-5-ethyluridine, 5-benzyl barbiturate, 5-benzyloxy-benzyl barbiturate, 5-benzyloxybenzyl-1-[(1-hydroxy-2-ethoxy)methyl] barbiturate, 5-benzyloxybenzylacetyl-1-[(1-hydroxy-2-ethoxy)methyl] barbiturate, 5-methoxybenzylacetylacyclobarbiturate, 5-ethynyluracil, bromovinyluracil, cyanodidhydropyridine, uracil, thymine, thymidine and benzyloxybenzyluracil. A nucleoside agent may contain one or more protecting groups (e.g. a hydroxyl protecting group, a bidentate diol protecting group, or a heterocyclic base protecting group) independently attached to any moiety(s) of the nucleoside agent.

Any convenient prodrugs of the subject nucleoside agents may be utilized in the subject methods. As described above, the term "prodrug" refers to a derivative of a nucleoside agent that requires a transformation within the body to release the active agent. In certain embodiments, the transformation is an enzymatic transformation. In certain embodiments, the transformation is a cyclization transformation. In certain embodiments, the transformation is a combination of an enzymatic transformation and a cyclization reaction. Prodrugs are frequently, although not necessarily, pharmacologically inactive until converted to the active agent.

In certain embodiments, the nucleoside agent is a ribonucleoside agent. In some embodiments, the nucleoside agent is described by formula (I):

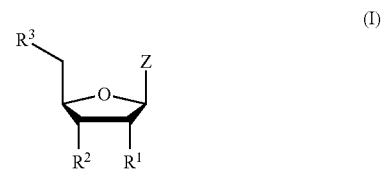

where: $R^1$, $R^2$ and $R^3$ are independently selected from any suitable substituents, such as H, halogen, OH, acyloxy, alkoxy, substituted alkoxy, a phosphorus containing group, thiol, thioalkoxy, substituted thioalkoxy, azido, amino, aminoacyloxy and substituted amino; and Z is a heterocyclic base moiety, such as a purine or a pyrimidine, or an analog thereof. A "phosphorus containing group" is a group that includes a phosphorus atom, such as any convenient phosphorus containing group or linkage utilized in oligonucleotides and oligonucleotide synthesis. Phosphorus containing groups of interest include, but are not limited to, phosphate, phosphate esters, thiophosphate, phosphoramidate, thiophosphoramidate, phosphite, phosphines, and the like. In certain instances of formula (I), $R^1$ is H, OH or a halogen (e.g., F). In certain cases of formula (I), $R^1$, $R^2$ and $R^3$ are independently selected from H, halogen, OH, OR, $NH_2$ or NHR, where R is an acyl, a substituted acyl, a phosphorus containing group, an alkyl or a substituted alkyl. In certain instances of formula (I), the agent includes a 3'-O phosphorus containing group (e.g., a phosphate) and/or a 5'-O phosphorus containing group (e.g., a phosphate).

In some instances, the nucleoside agent is a ribonucleoside agent selected from a 6-deazapurine ribonucleoside and a 6-azauridine ribonucleoside. In some cases, the ribonucleoside agent is a 6-deazapurine ribonucleoside. A 6-deazapurine ribonucleoside includes a ribose sugar moiety (e.g., as described herein) connected to a 6-deazapurine heterocyclic base via a glycosidic linkage. A 6-deazapurine heterocyclic base is a purine analog where the 6-amino group is replaced with a non-amino substituent. In some instances, the 6-deazapurine heterocyclic base bears a substituent at the 6-position selected from H, acyl, alkyl, alkenyl, alkynyl, aryl, heteroaryl, halogen, hydroxy, alkoxy, aryloxy, heteroaryl oxy, sulfonyl, sulfonate, carboxy, thiol, nitro, cyano and substituted versions thereof.

In some embodiments, the nucleoside agent is a 6-deazapurine ribonucleoside described by formula (II):

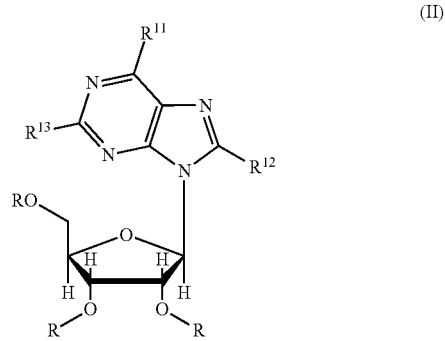

where: each R is independently selected from, H, acyl, aminoacyl, alkyl, substituted alkyl, a phosphorus containing group and an enzymatically cleavable group; and $R^{11}$, $R^{12}$ and $R^{13}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. In some embodiments of formula (II), $R^{11}$ is not an amino or a substituted amino. In certain embodiments of formula (II), each R is independently H or acyl, $R^{11}$ is halogen and $R^{12}$ and $R^{13}$ are hydrogen. In certain embodiments of formula (II), each R is H. In certain embodiments of formula (II), each R is acyl. In certain embodiments of formula (II), each R is acetyl. In certain instances of formula (II), each R is independently selected from H, an acyl, a substituted acyl, a phosphorus containing group, an alkyl or a substituted alkyl. In certain instances of formula (II), the agent includes a 3'-O phosphorus containing group (e.g., a phosphate) and/or a 5'-O phosphorus containing group (e.g., a phosphate).

In certain instances, the ribonucleoside agent is 6-Chloropurine riboside (i.e., HD103) which has the following structure:

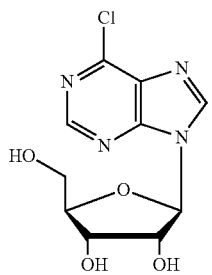

In certain instances, the ribonucleoside agent is a 6-azauridine ribonucleoside. As used herein, the terms "6-azauridine ribonucleoside", and "6-azauracil riboside" are used interchangeably. A 6-azauridine ribonucleoside includes a ribose sugar moiety (e.g., as described herein) connected to a 6-azauracil heterocyclic base via a glycosidic linkage. A 6-azauracil heterocyclic base is a pyrimidine analog that include a nitrogen atom at the 6 position of the ring instead of a carbon atom. In some instances, the 6-azauracil heterocyclic base bears a substituent at the N3 and/or C5 positions selected from H, acyl, alkyl, alkenyl, alkynyl, aryl, heteroaryl, halogen, hydroxy, alkoxy, aryloxy, heteroaryl oxy, sulfonyl, sulfonate, carboxy, thiol, nitro, cyano and substituted versions thereof. In certain instances, the 6-azauracil heterocyclic base may be referred to as a 6-azathymine heterocyclic base, when a methyl substituent is included at the C5 position.

In some embodiments, the 6-azauridine ribonucleoside is described by formula (III):

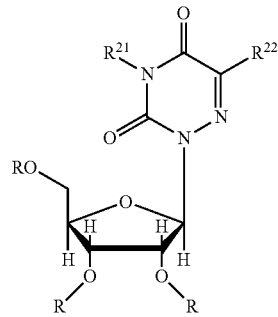

where: each R is independently selected from, H, acyl, aminoacyl, alkyl, substituted alkyl, a phosphorus containing group and an enzymatically cleavable group; and $R^{21}$ and $R^{22}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. In certain instances of formula (III), each R is independently selected from H, an acyl, a substituted acyl, a phosphorus containing group, an alkyl or a substituted alkyl. In certain embodiments of formula (III), each R is independently H or acyl, $R^{21}$ is hydrogen and $R^{22}$ is hydrogen. In certain embodiments of formula (III), each R is H. In certain embodiments of formula (III), each R is acyl. In certain embodiments of formula (III), each R is acetyl. In certain embodiments of formula (III), $R^{21}$ is selected from hydrogen, alkyl, substituted alkyl, acyl and substituted acyl. In certain embodiments of formula (III), $R^{21}$ is hydrogen. In certain embodiments of formula (III), $R^{22}$ is selected from hydrogen, alkyl, substituted alkyl, halogen, alkoxy, substituted alkoxy, acyl and substituted acyl. In certain embodiments of formula (III), $R^{22}$ is hydrogen. In certain instances of formula (III), the agent includes a 3'-O phosphorus containing group (e.g., a phosphate) and/or a 5'-O phosphorus containing group (e.g., a phosphate).

In certain instances, the ribonucleoside agent is 6-Azauridine (i.e., HD101) having the following structure:

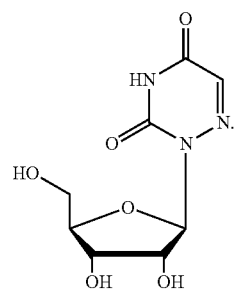

As mentioned above, the nucleoside agent may be provided as a prodrug. Such prodrugs are in general functional derivatives of the compounds that are readily convertible in vivo into the required compounds. Prodrugs include esters that hydrolyze in vivo (e.g., in the human body) to produce an active nucleoside agent. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates. An example of a prodrug finding use in embodiments of the invention is the HD101 prodrug (−)—6-Azauridine 2',3',5'-Triacetate (i.e., HD106), having the following structure:

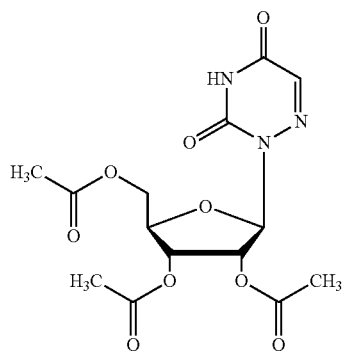

As reviewed above, the subject methods result in reduction in the deleterious activity of an extended trinucleotide repeat gene in a target cell or cells, where the target cell(s) may be in vitro or in vivo. In certain embodiments, the subject methods result in reduction in toxicity of a target gene, e.g., via a reduction in aggregation of a protein encoded thereby, in a target cell(s). In certain embodiments, the methods result in enhancement in function of a protein encoded by a target gene.

The above methods find use in a variety of different applications. Certain applications are now reviewed in the following Utility section.

Utility

The subject methods find use in a variety of applications in which reduction of the deleterious activity of gene containing a mutant extended trinucleotide repeat domain is desired. As such, aspects of the invention include reducing toxicity of and/or enhancing functionality of a protein encoded by such a gene, as described herein, in any subject in need thereof, e.g., a subject that has been diagnosed with a condition that can be treated by effecting one or more of the above outcomes in the subject. Of interest is use of the methods and compositions of the invention to modify the progression of disease conditions associated with the deleterious activity of genes containing mutant extended trinucleotide repeat domains. The phrase "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition). Specific disease conditions in which the methods and compositions of the invention find use include, but are not limited to polyQ disease conditions, such as Spinocerebellar ataxia type 1, Spinocerebellar ataxia type 2, Spinocerebellar ataxia type 3, Spinocerebellar ataxia type 7, Spinocerebellar ataxia type 17, Dentatorubral pallidoluysian atrophy, Spinal and bular muscular atrophy, and Huntington's Disease.

In some instances, practice of methods of the invention results in treatment of a subject for a disease condition. By treatment is meant at least an amelioration of one or more symptoms associated with the disease condition afflicting the subject, where amelioration is used in a broad sense to refer to at least a reduction in the magnitude of a parameter, e.g., symptom, associated with the pathological condition being treated, such as loss of cognitive function, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition. Treatment may also manifest in the form of a modulation of a surrogate marker of the disease condition, e.g., as described above.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs and rats), and primates (e.g., humans, chimpanzees and monkeys). In some embodiments, the host is human.

Combination Therapies

Active agents of the invention can be administered to a subject alone or in combination with an additional, i.e., second, active agent. As such, in some cases, the subject method further comprises administering to the subject at least one additional compound. Any convenient agents may be utilized, including compounds useful for treating viral infections. The terms "agent," "compound," and "drug" are used interchangeably herein. For example, selective SPT4 inhibitory nucleoside agents can be administered alone or in conjunction with one or more other drugs, such as drugs employed in the treatment of polyQ diseases. In some embodiments, the method further includes coadministering concomitantly or in sequence a second agent. Possible second agents of interest include, but are not limited to, dopamine-depleting agents (e.g., tetrabenazine (Xenazine) or reserpine); dopamine-receptor antagonists (e.g., neuroleptic), amantadine, levetiracetam, anticonvulsants (e.g., valproic acid), antipsychotic drugs, such as risperidone, haloperidol (Haldol) and clozapine (Clozaril); antiseizure drugs, benzodiazepines (e.g., clonazepam (Klonopin)) and antianxiety drugs such as diazepam (Valium); antidepressants including such drugs as escitalopram (Lexapro), fluoxetine (Prozac, Sarafem) and sertraline (Zoloft); laquinimod, pridopidine, rasagiline, a pan-PPAR agonist (e.g., bezofibrate); nucleic acid silencing agents, e.g., RNA silencing agents targeting, e.g., a HTT single nucleotide polymorphism (SNP); and the like. Antisense oligonucleotides or interfering RNAs directed against SUPT4H may also be part of a combination therapy.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present invention means administration of the drug and nucleoside agent at such time that both the known drug and the composition of the present invention will have a therapeutic effect. Such concomitant administration may involve concurrent (i.e. at the same time), prior, or subsequent administration of the drug with respect to the administration of a subject nucleoside agent. Routes of administration of the two agents may vary, where representative routes of administration are described in greater detail below. A person of ordinary skill in the art would have no difficulty determining the appropriate timing, sequence and dosages of administration for particular drugs and nucleoside agents of the present invention.

In some embodiments, the compounds (e.g., a nucleoside agent and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further include dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific nucleoside agent, the nature of the delivery vehicle, and the like. Preferred dosages for a given nucleoside agent are readily determinable by those of skill in the art by a variety of means.

Kits & Systems

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. In some embodiments, the subject system or kit includes a nucleoside agent (e.g., as described herein) and a second active agent (e.g., as described herein). In certain instances, the second active agent is selected from: a dopamine-depleting agent (e.g., tetrabenazine or reserpine), a dopamine-receptor antagonist (e.g., neuroleptic), amantadine, levetiracetam, an anticonvulsant (e.g., valproic acid), a benzodiazepine agent (e.g., clonazepam), laquinimod, pridopidine, rasagiline, a pan-PPAR agonist (e.g., bezofibrate), an antipsychotic agent (e.g., risperidone or haloperidol) and a RNA silencing agent targeting a HTT single nucleotide polymorphism (SNP). Kits and systems for practicing the subject methods may include one or more pharmaceutical formulations. As such, in certain embodiments the kits may include a single pharmaceutical composition, present as one or more unit dosages, where the composition may include one or more nucleoside compounds (e.g., as described herein). In some embodiments, the kit may include two or more separate pharmaceutical compositions, each containing a different active agent, at least one of which is a nucleoside compound (e.g., as described herein).

Also of interest are kits and systems finding use in the subject methods, e.g., as described above. Such kits and systems may include one or more components of the subject methods, e.g., nucleoside agents, cells, vectors encoding proteins of interest, enzyme substrates, dyes, buffers, etc. The various kit components may be present in the containers, e.g., sterile containers, where the components may be present in the same or different containers.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Experimental

The following methods and materials may be adapted for use in assessing the subject agents and compositions.

I. Identification of Spt4/Spt5 Protein/Protein Interaction Inhibitors

A. Bimolecular Fluorescence Complementation (BiFC) Assay

Materials and Methods a. Plasmid Construction i. pHA-Supt4h-YC & pFLAG2-NGN-YN

Human Supt4h and Supt5hNGN were fused in-frame with the YC and YN respectively. The YN and YC represent the N- and C-terminal domain of yellow fluorescent protein Venus. To prevent a change in protein folding caused by the conjugation of two polypeptides (Kerppola, "Design and implementation of bimolecular fluorescence complementation (BiFC) assays for the visualization of protein interactions in living cells," Nature protocols (2006) 1:1278-1286), a protein linker containing additional 10 amino acid residues was included in the fusion protein. Also, extra amino acids GSHM were incorporated into the Supt5hNGN to increase its protein stability (Wenzel et al., "Crystal structure of the human transcription elongation factor DSIF hSpt4 subunit in complex with the hSpt5 dimerization interface," The Biochemical journal (2010) 425:373-380). Supt4h, NGN, YC, and YN were amplified by PCR to generate DNA fragments containing the nucleotide sequence of protein linker. Supt4h and NGN PCR products then were mixed with the PCR product of YN or YC for secondary overlapping PCR. Finally, the resulting Supt4h-YC and NGN-YN DNA fragment was cloned into plasmid vector pcDNA3-HA and pFLAG-CMV-2 respectively.

ii. pTRE-HA-Supt4h-YC-FLAG-NGN-YN & pTRE-HA-Venus

The HA-Supt4h-YC and FLAG-NGN-YN fragments were amplified by PCR using plasmid constructs described above and sub-cloned individually into the pTRE-tight-BI vector (Clontech Laboratories), which contain a bi-directional CMV promoter under the control of tetracycline. The coding sequence of yellow fluorescence protein Venus with a HA-epitope in its N-terminus was PCR-amplified and cloned into the vector to generate pTRE-HA-Venus.

b. Cell Culture

Tet-on HeLa cells (Clontech Laboratories), and stable line 2-PN4 and 21-VS were cultured in DMEM (Gibco) supplemented with 10% Tet-off fetal bovine serum (Gibco) at 37° C. with 5% $CO_2$. Hdh Q7/Q7 (mouse), Hdh Q111/Q111 (mouse) were cultured in DMEM (HyClone) supplemented with 10% fetal bovine serum at 33° C. with 5% C02.

c. Stable Cell Line

Tet-on HeLa cells were transfected with linearized pTRE-HA-Supt4h-VC-Flag-NGN-VN plasmid construct using LipofectAMINE 2000 (Invitrogen). After transfection, cells were cultured initially in growth medium containing puromycin (1 µg/ml) and then selected for clones that show YFP fluorescence in the presence of tetracycline (4 µg/ml). The stable line having the strongest fluorescence signal was isolated and designated as 2-PN4. Likewise, 21-VS stable line was created using pTRE-HA-Venus.

d. Measurement of Fluorescence Intensity

Stable lines 2-PN4 and 21-VS were pre-cultured in 6-well plates, followed by an incubation of Doxycycline (4 µg/ml) together with various concentrations of chemical compounds for 24 hr. Cells were washed with PBS (Sigma) and monitored by microscope (20× magnification). Photos were taken using Nikon D500 camera with a setting of ISO 1600, shutter 1/200 for the light images, and shutter ½ for the fluorescence images. For quantification of fluorescence intensity, 5 photos with similar cell number were taken and the fluorescence signal was measured by Metamorph software individually. The average of overall fluorescence signal was determined and compared to the one observed in DMSO-treated control sample.

e. Antibodies

Antibodies against α-tubulin (DM1A, Sigma), FLAG-epitope (F4041, Sigma), and HA-epitope (16B12, Covance) were purchased.

f. Western Blotting

As described (Liu et al., "Spt4 is selectively required for transcription of extended trinucleotide repeats," Cell (2012) 148:690-701), equal amounts of protein were resolved by electrophoresis on 12% sodium dodecyl sulfate (SDS)-polyacrylamide gels, and transferred onto nitrocellulose membranes (nitrocellulose, Waterman 0.45 µM, NBA085C). After blocking with 5% low-fat milk in Tris-buffer saline containing 0.1% Tween-20, membranes were probed with primary antibodies, incubated with a horseradish peroxidase (HRP)-conjugated secondary antibody, and detected by ECL reagent (enhanced chemiluminescence, PerkinElmer).

g. Co-Immunoprecipitation

2-PN4 cells, following a treatment of 6CR ($C_f$=20 µM) for 36 hr, were lysed with modified RIPA buffer (50 mM Tris-HCl [pH 7.5], 150 mM NaCl, 1% NP-40, 1% sodium deoxycholate), supplement with 1 mM $Na_3VO_4$, 1 mM DTT, 1 mM PMSF and protease inhibitor cocktail (Sigma). The collected protein lysates (1 mg) were diluted with modified RIPA buffer to a final volume of 0.5 ml and then incubated with anti-HA antibodies (1 µg) overnight. Following incubation with protein A agarose beads (Millipore) for another 6 hr, the beads were washed twice with modified RIPA buffer containing 20 µM 6CR. All of these performances were carried out at 4° C. For detection of proteins that coprecipitated with HA-Supt4h-YC, the immunocomplex was fractionated by SDS-PAGE, followed by Western blotting analysis with anti-HA and anti-FLAG antibodies.

h. RT-PCR

Total RNA was extracted from murine neuronal cells using TRI Reagent (Sigma). For cDNA conversion, 2 µg of total RNA was mixed with 5 µM random primer, 5 µM SnRNA U6 rt-PCR primer and 500 µM dNTPs, incubated at 65° C. for 5 min and then chilled on ice. After addition of First-Strand Buffer, DTT ($C_f$=10 mM) and 1 µl reverse transcriptase (Invitrogen), the reaction was carried out at 42° C. for 1 hr. Equal volumes of cDNA products were PCR amplified and resolved on 2.5% agarose gels to determine the abundance of Htt transcripts after normalization with U6 or 18S ribosomal RNA.

2. Results

Figure 2:
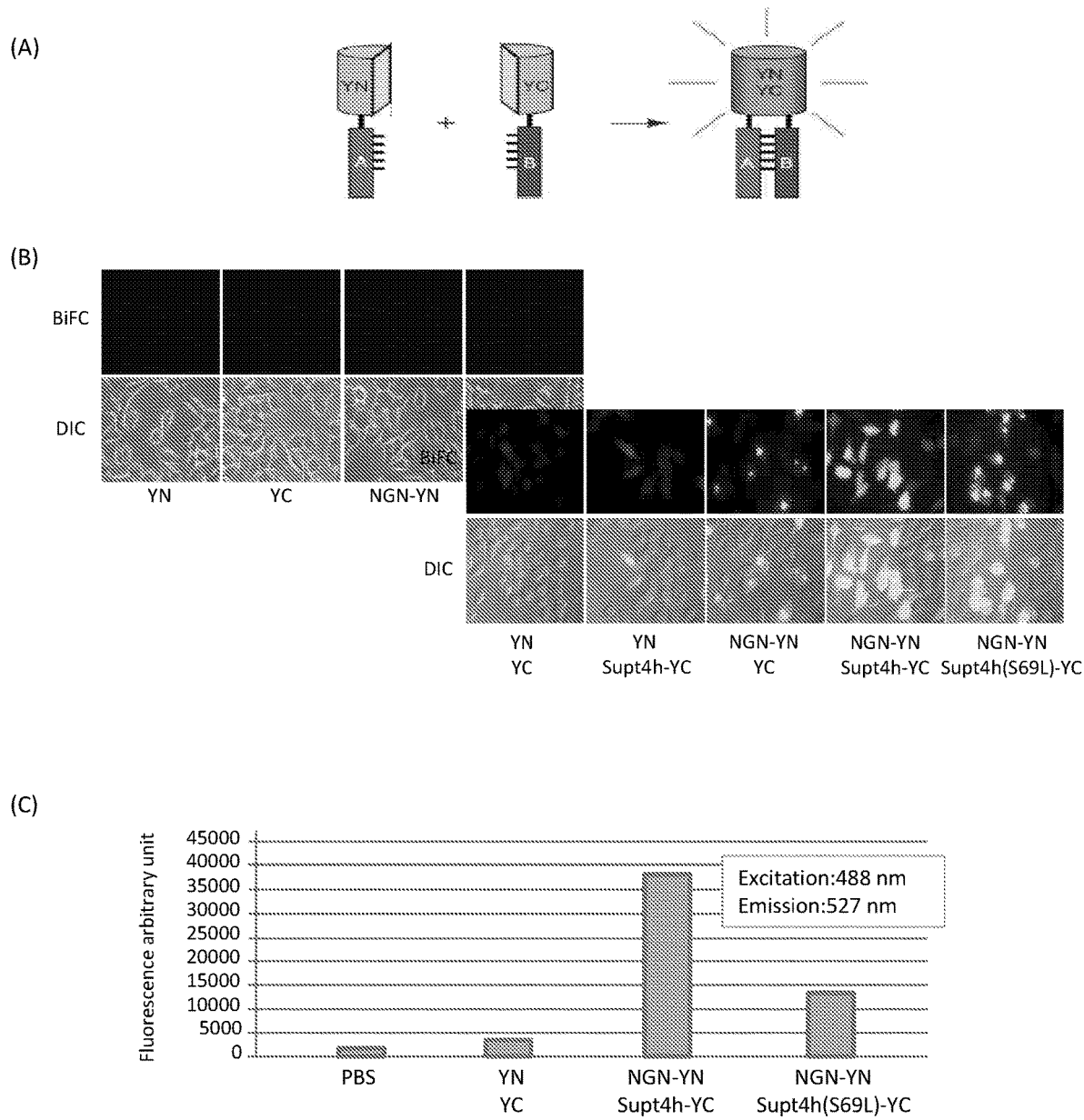
FIGS. 2A to 2C. The Bimolecular Fluorescence Complementation (BiFC) is employed to monitor the Supt4h/Supt5h NGN complex formation.

To monitor the interaction between Supt5h NGN and Supt4h in living cells, a method of bimolecular fluorescence complementation (BiFC) assay (Hu et al., "Visualization of interactions among bZIP and Rel family proteins in living cells using bimolecular fluorescence complementation," Mol. Cell. (2002) 9:789-798) was employed. The human Supt5h NGN and Supt4h were fused to distinct fragments of yellow fluorescent protein (YFP). For YFP complementation to occur, the YN and YC fragments have to be in close proximity (FIG. 2A). The crystal structure of NGN/Supt4h complex (Wenzel et al., 2009, supra) revealed that the C-termini of these proteins are spatially aligned together. Therefore, in our design, the YN and YC fragments were fused to the C-terminus of each of these proteins to promote YFP complementation and subsequent production of fluorescent signal.

The assay was initially tested in HeLa cells transiently expressing the YN, YC, NGN-YN, Supt4h-YC alone or in combination of these proteins. NGN-YN is a genetic engineered protein in which Supt5h NGN domain is fused to YFP YN, whereas Supt4h-YC is a fusion protein comprised of Supt4h and YFP YC. We found that YN and/or YC expression does not generate and evident fluorescence signal; however, a strong fluorescent signal is detectable when NGN-YN and Supt4h-YC are expressed concurrently (FIG. 2B). More importantly, the fluorescence signal is greatly reduced (FIG. 2C) when a Supt4h point mutation (S69L) is introduced into the interaction assay. The amino acid residue of Serine 69 in Supt4h plays an essential role in stabilizing the interaction interface between Supt4h and Supt5h NGN, and the Serine to Leucine substitution results in a compromised Supt4h/NGN interaction. Therefore, these data indicate that the complementation of YFP is dependent on the interaction of Supt4h and Supt5h NGN per se, and inhibition of such interaction is detectable by a decrease of fluorescence signal in the assay.

For the purpose of high-throughput drug screening, based on the BiFC method as mentioned above, we have created a stable cell line that co-expresses NGN-YN and Supt4h-YC under the control of a tet-on inducible promoter. Because pre-existing complemented YFP molecules have a very low dissociation rate once the YN and YC fragments are bound to each other (Hu et al., "Visualization of interactions among bZIP and Rel family proteins in living cells using bimolecular fluorescence complementation," Mol Cell. (2002) 9:789-798), in our design, the engineered proteins are induced by doxycycline at the same time when test compounds are added into the cultured cells. If the complementation that is driven by NGN and Supt4h interaction is inhibited by a given test compound, the de novo YFP fluorescence signal is affected. To exclude the possibility that the reduction of YFP fluorescence is due to a negative impact on the tet-on inducible promoter or on the functionality of YFP, another tet-on inducible cell line that expresses an intact functional YFP is included as a control.

Figure 3:
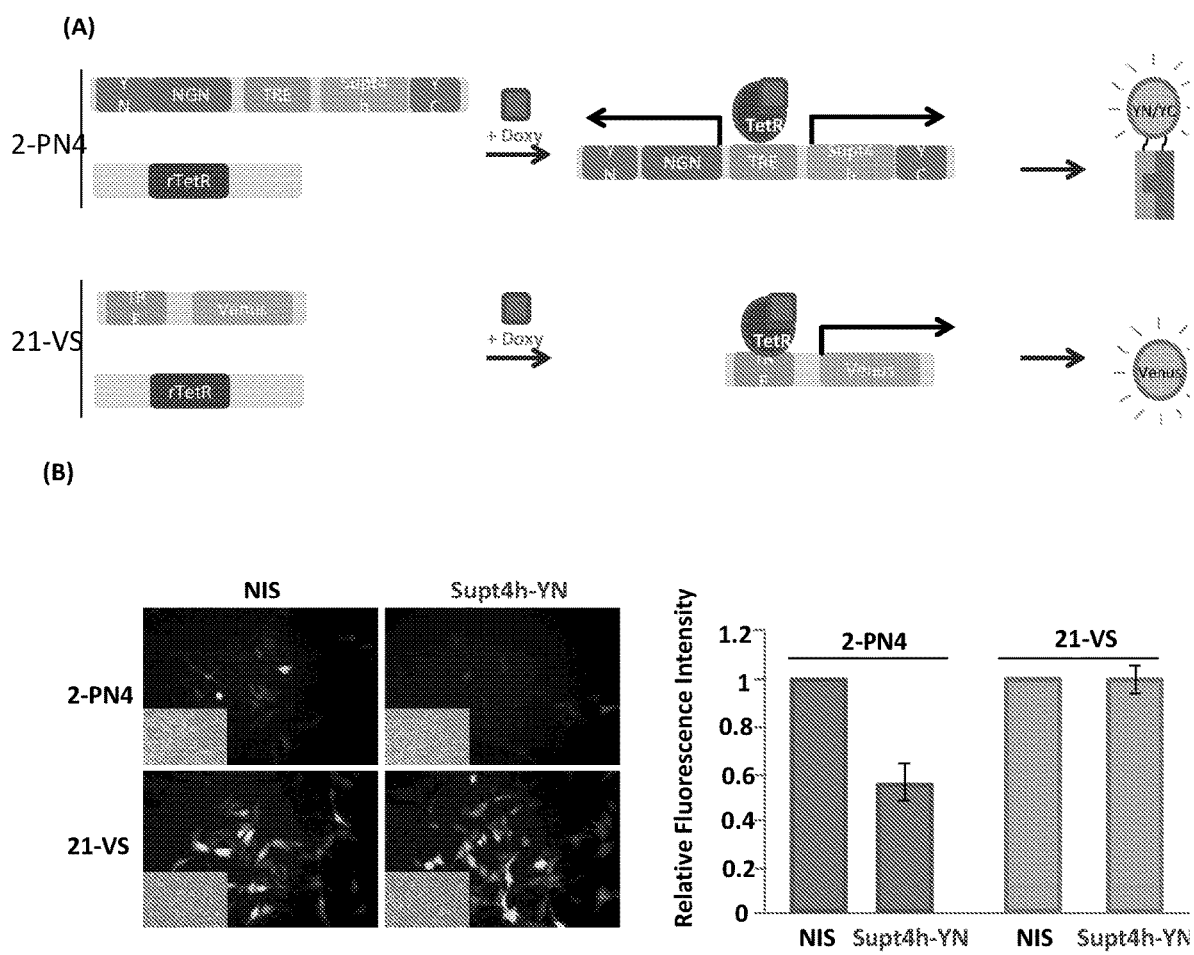
FIGS. 3A to 3B. 2-PN4 and 21-VS stable cell lines are created for identification of compounds that inhibit the interaction between NGN-YN and Supt4h-YC.

We have generated and characterized a stable cell line, designated as 2-PN4, that expresses NGN-YN and Supt4h-YC concurrently and produces YFP fluorescence signal in a tetracycline-dependent manner (FIG. 3A). In addition, we have generated a control cell line 21-VS (FIG. 3A) that produces YFP fluorescence signal directly without the need of YN/YC complementation. Using these two stable cell lines, we found that ectopic expression of Supt4h-YN results in a decrease of fluorescence signal from 2-PN4, but not 21-VS cells (FIG. 3B). Supt4h-YN is capable of interacting with NGN-YN and interfering with the YFP complementation driven by Supt4h-YC and NGN-YN. Therefore, our data demonstrates that the fluorescence signal of 2-PN4 is susceptible to the negative effect that prevents the interaction between Supt4h-YC and NGN-YN. This data also shows that the stable line 2-PN4, together with the use of 21-VS, is suitable for identification and characterization of compounds that specifically inhibit the complex formation of Supt4h/5h.

Figure 4:
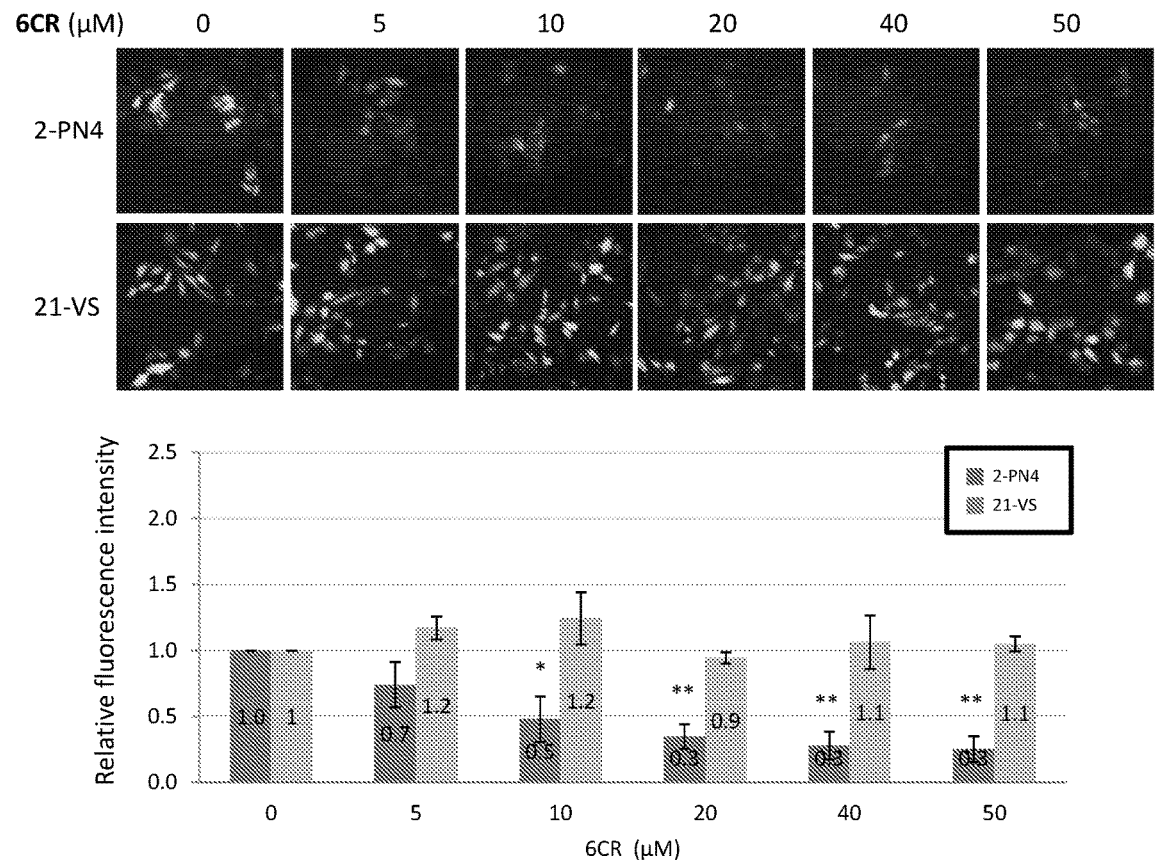
FIGS. 4A to 4D. 6-chloro purine riboside (6CR) inhibits Supt4h-YC and NGN-YN interaction in 2-PN4 cells and reduces the expression of mutant Htt gene in murine neuronal cells.
Figure 4:
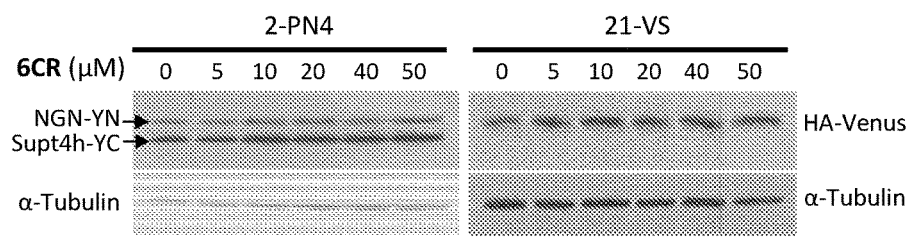
Figure 4:
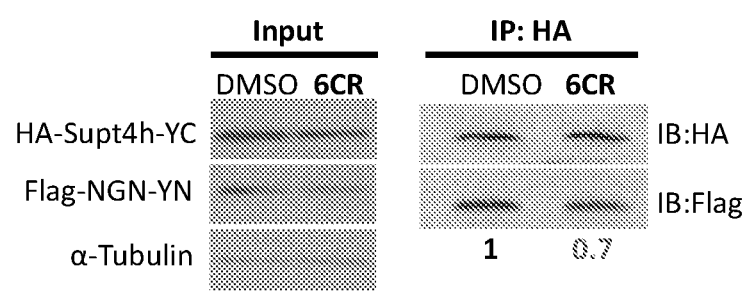
Figure 4:
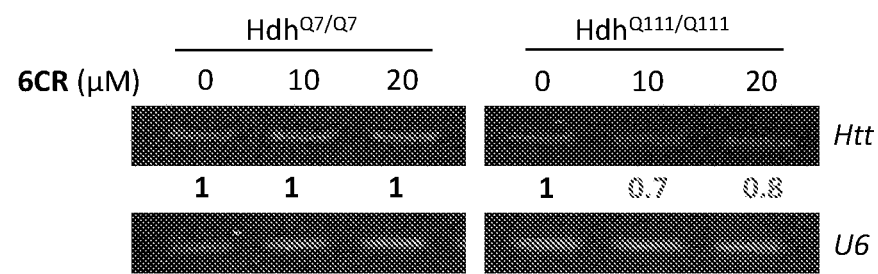

Through high-throughput screening, several nucleoside compounds were identified. The effects of these compounds on the fluorescence signal of 2-PN4 and 21-VS cells, along with the influence of these compounds on the protein interaction of Supt4h-YC and Supt5h NGN-YN, were further characterized. We found that 6-chloro purine riboside (6CR) reduces the fluorescence signal of 2-PN4 cells in a concentration-dependent manner. The fluorescence intensity is decreased to half of control sample at 10 µM of 6CR, and to a greater extent at higher doses (FIG. 4A). While such inhibition is evident in 2-PN4 cells, the fluorescence signal of 21-VS cells is not altered by 6CR under the same experimental conditions (FIG. 4A), demonstrating the inhibitory action of 6CR is specific to the fluorescence signal of BiFC. In 2-PN4 cells, 6CR does not interfere with the protein expression of Supt4h-YC and NGN-YN (FIG. 4B); however, it does lower the complex formation of these two proteins (FIG. 4C). These findings show that the reduction of BiFC is mediated through a decrease of Supt4h/NGN protein-protein interaction in cells subjected to a treatment of 6CR. In our earlier investigation (Liu et al., 2012, supra), we showed that Supt4h deficiency or compromised Supt4h/Supt5h complex formation results in a decrease of transcription of genes containing expanded tri-nucleotide repeats, such as mutant huntingtin (Htt) gene. Therefore, the inhibitory effect of 6CR on the expression of Htt gene was further examined in murine neuronal cell lines. We found that the Htt mRNA transcribed from mutant allele is down-regulated by 6CR, but such down-regulation is not detectable in cells expressing homozygous allele of wild-type Htt (FIG. 4D). These results show that 6CR, by targeting the transcription elongation complex Supt4h/Supt5h, specifically reduces the expression of gene that is responsible for the pathogenesis of HD.

Figure 5:
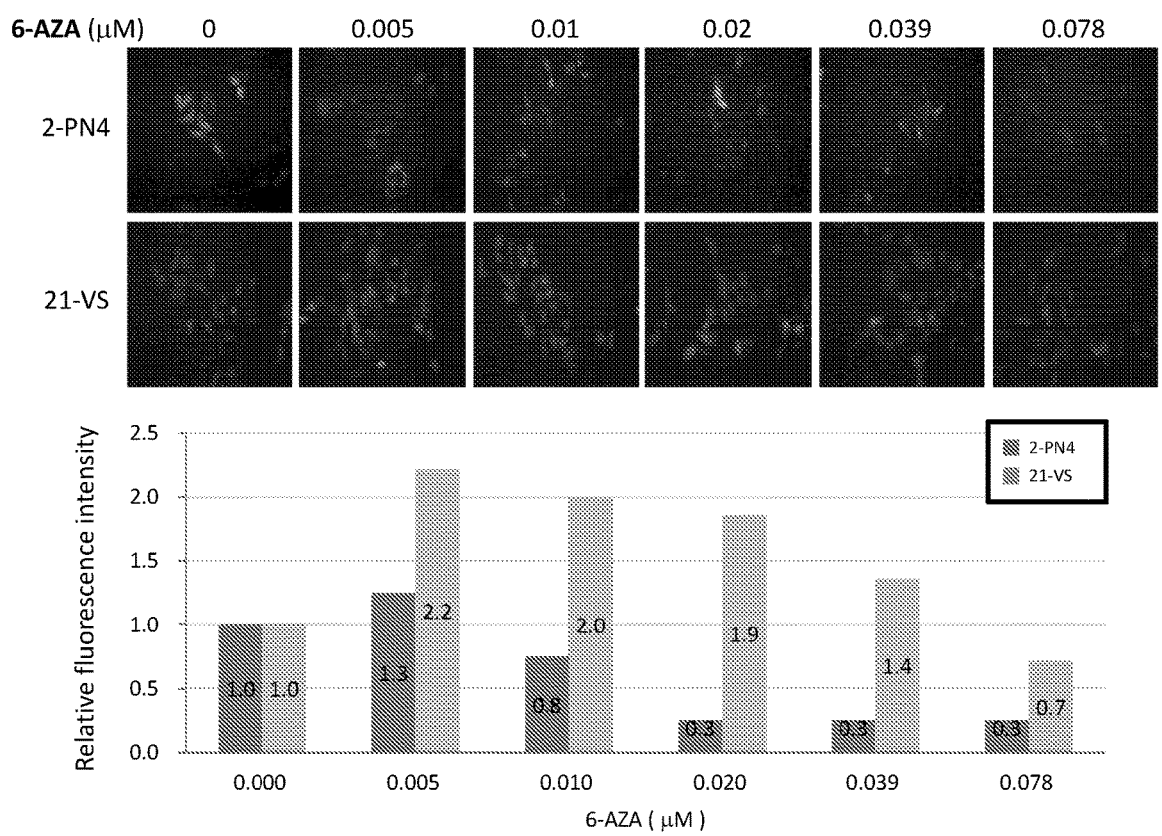
FIGS. 5A to 5C. 6-Azauridine (6-AZA) inhibits the fluorescence signal of BiFC in 2PN-4 cells and down-regulates the expression of mutant Htt gene in murine neuronal cells.
Figure 5:
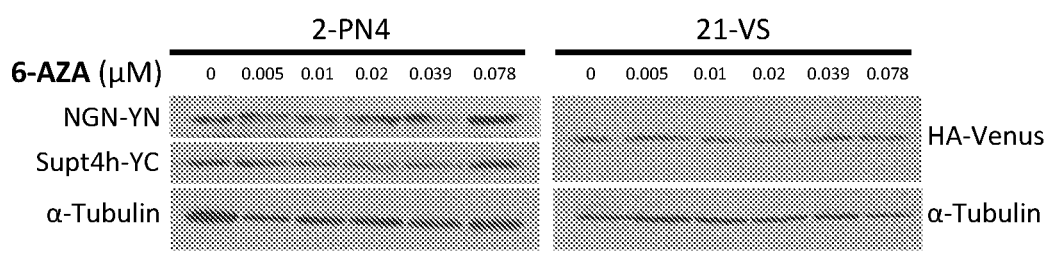
Figure 5:
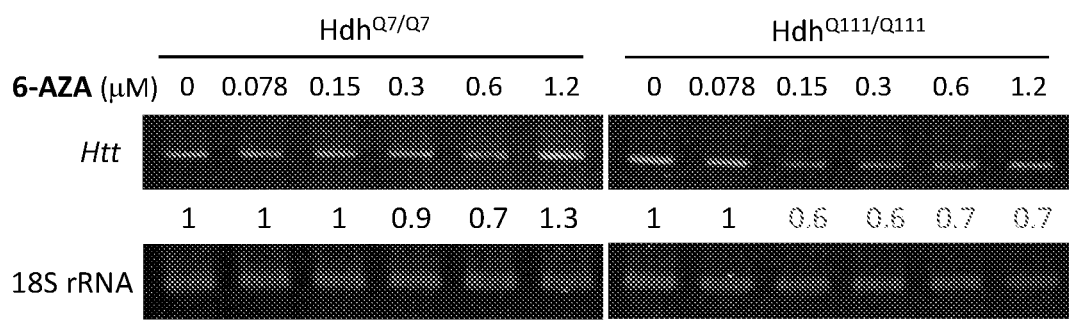

6-Azauridine (6-AZA) also inhibits the fluorescence signal of BiFC in 2-PN4 cells. At the concentration of 0.02 µM, 6-AZA reduces approximately 70% of BiFC signal compared to mock controls (FIG. 5A). While the extent of BiFC reduction has reached its plateau, the fluorescence of 21-VS cells is markedly affected by 6-AZA in a higher concentration (FIG. 5A). Analogous to 6CR, 6-AZA does not decrease the BiFC signal via a change in the protein level of Supt4h-YN and NGN-YN (FIG. 5B). Additionally, 6-AZA down-regulates the expression of mutant, but not wild-type Htt allele (FIG. 5C). These findings show that both 6CR and 6-AZA possess a similar characteristic in suppressing the interaction of Supt4h and Supt5h, which is accompanied by a decrease in the expression of genes containing expanded CAG repeats.

B. Split *Gausssia Luciferase Complementation Assay*
1. Material and Methods
a. Plasmid Construction
i: pNBR-X1-Supt4-Gluc1 and pNEBR-X1-NGN-Gluc2

The HA-Supt4h and Flag-NGN fragments were amplified by PCR using the plasmid pHA-Supt4h-YC and pFlag-NGN-YN and sub-cloned individually into pcDNA3.1-Gluc1 and pcDNA3.1-Gluc2 (described in "A highly sensitive protein-protein interaction assay based on *Gausssia* luciferase" published at Nat Methods. 2006 December; 3(12):977-9. Epub 2006 Nov. 12). Then HA-Supt4h-Gluc1 and Flag-NGN-Gluc2 were amplified by PCR and inserted to pNEBR-X1-Hygro (New England BioLabs), which contain RheoSwitch responsive element under the control of RheoSwitch ligand.
Ii: pNEBR-X1-Supt4h-G1-NGN-G2

PCR products containing the sequence from 5XRE to polyA in pNEBR-X1-NGN-G2 were inserted to pNEBR-X1-Supt4h-G1 at PciI site to generate Supt4h-G1 and NGN-G2 bidirectional under their own RheoSwitch responsive element and polyA in the same plasmid.
Iii: pEGFPC1-Q22 and pEGFPC1-Q44

CAG repeats and part of the flanking region in the first exon of Htt gene were PCR amplified from cDNA of HD patient lymphoblastoid cells containing one normal and one mutant allele (Q22 and Q44) with additional flanking restriction enzyme sites NheI. The PCR fragments were than in-frame fused with pEGFP-C1 at the end of the EGFP gene to express polyQ tagged GFP.
b. Stable Cloned Cell Line i: 293-R1 is a cloned cell which was engineered to constitutively express RSL1 receptor/activator by transfecting HEK 293 cells with pNEBR-R1 plasmid (New England BioLabs) and selected with Blasticidin.

ii: M2-8 is a cloned 293-R1 cell which can inducibly express pNEBR-X1-Supt4h-G1-NGN-G2 by addition of RSL1. Two point mutations (M431 and M1101) were introduced to the GL1 and GL2 for better stability according to "A high-throughput cell-based *Gaussia* luciferase reporter assay for identifying modulators of fibulin-3 secretion" published on J Biomol Screen. 2013 July; 18(6):647-58. The cell line was selected by Hygromycin.
c. Cell Culture and Transfection Condition All the HEK-293 cells and derivative cell clones were maintained in DMEM containing 10% FBS plus corresponding antibiotics (250 µg/ml hygromycin B, 10 µg/ml blasticidin or both) at 37° C., 5% $CO_2$. All the transfections were done by using lipofectamine 2000 (Invitrogen) according to the manufacture's direction.
d. Bioluminescence Assay in Cell Lysates Plasmids harboring the Gluc1 and Gluc2 were co-transfected in a 1:1 ratio into 293-R1 cells plated on tissue culture treated 24-well plates using Lipofectamine 2000 according to the manufacturer's instruction. For stable cell M2-8, the cells were plated into 96 well or 384 well white plate directly. 24 hours later, RheoSwitch ligand together with/without test compound was added to the cells for induction/drug treatment. After 24 hr, the cells were washed with PBS and the plate was put in −20° C. freezer for overnight. After taking out the plate from freezer, lysis buffer (30 mM Tris-HCl, pH 8.0, 5 mM NaCl, 0.1% Triton X-100) with 10 µg/ml native coelenterazine (Nanolight Technology) was immediately added to the cells. The cells were lysed at room temperature for one hour in dark. After shaking for about 1 min, 40 µl of cell lysate were transfer to a white 96 well plate. For M2-8 in white micro plate, no transfer was needed. Signal intensities (integrated 100 ms) were read on Tecan Infinite M200 or M1000.
e. Western Blot Analysis Cell samples were lysed in 30 mM Tris-HCl, pH 8.0, 5 mM NaCl, 0.1% Triton X-100 for 10 min on ice. The supernatants from spinning (14 k rpm for 10 min) were collected. The protein concentrations were determined by BCA assay (Pierce, ThermoFisher). Equal amounts of protein were loaded onto 4-12% gel. After electrophoresis, the gels were transferred to nitrocellulose membranes by wet transfer at 35V for 16 hr. The protein level of mutant HTT, total HTT and tubulin were determined by immunoblotting with anti-poly Glutamine (MAB1574 from Millipore), anti-Huntingtin protein (MAB2166 from Millipore) and anti-alpha tubulin (AJ1034a from ABGENT). Blots were imaged on a Li-Cor Odyssey infrared imager. The bands intensities were determined by Li-Cor Odyssey software.
2. Results To monitor the interaction between Supt5h NGN and Supt4h in living cells, a protein-fragment complementation assay (PCA) with split *Gaussia princeps* luciferase (GLuc) as a reporter (Remy & Micjhmick "A highly sensitive protein-protein interaction assay based on *Gausssia* luficerase" Nature Methods (2006) 3: 977-979) was used. When used in the PCA, *Gausssia* luciferase is a sensitive reporter which allows the detection of protein-protein interactions in even sub-endogenous expression, and the interaction of the two split GLuc is fully reversible.

Figure 6:
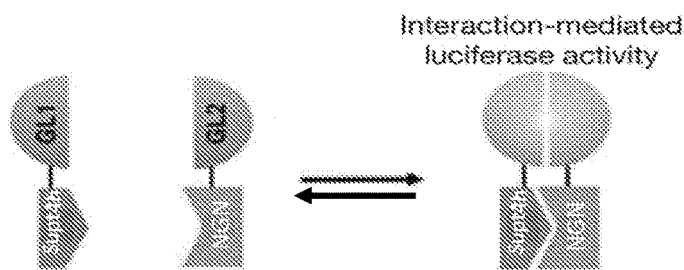
FIGS. 6A to 6D provide an experimental strategy for detecting interaction between Supt4h1 and the NGN domain of Supt5 using a split luciferase complementation assay.
Figure 6:
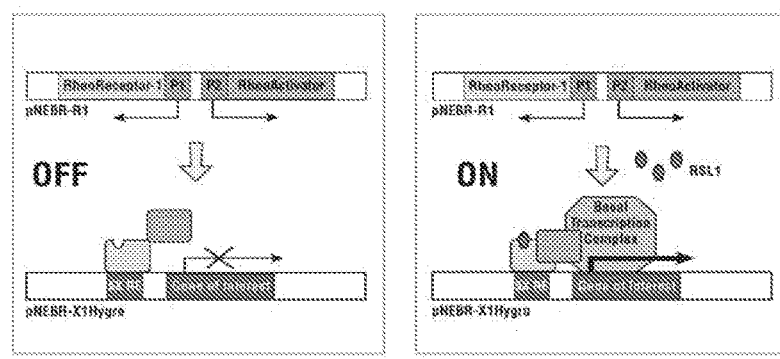
Figure 6:
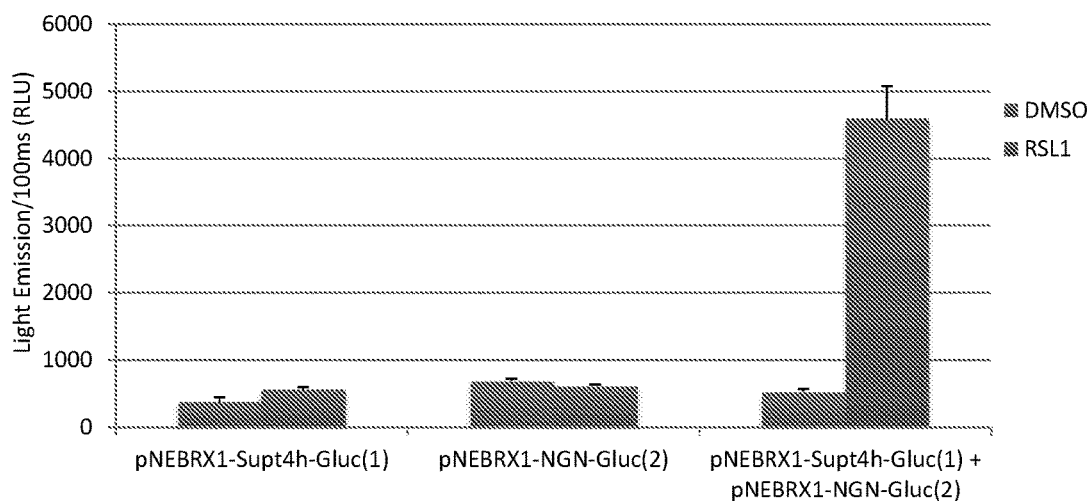
Figure 6:
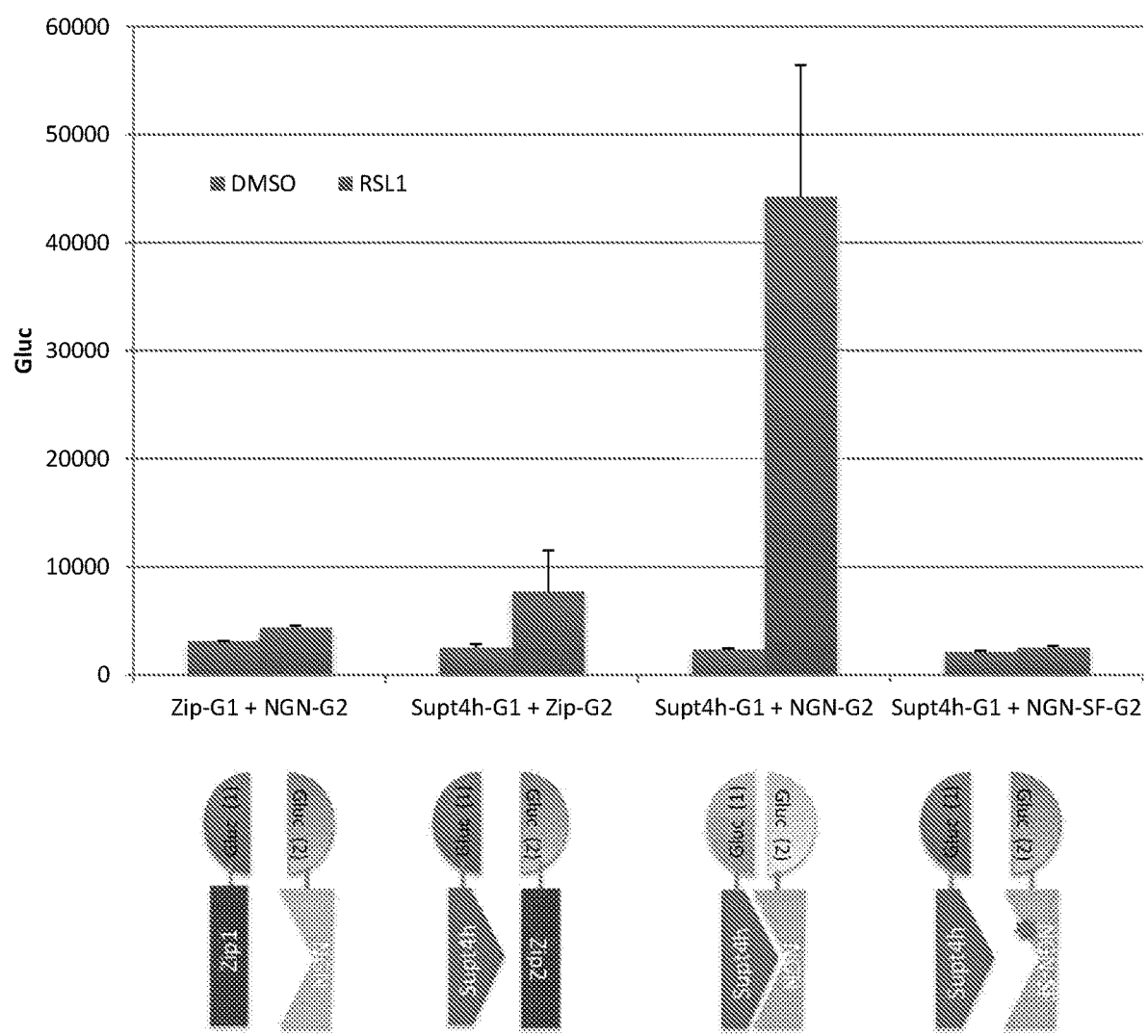

Human genes encoding the Supt4h protein or the amino terminal domain of Supt5h (NGN) were each fused with genes that encode subunits (GLuc1 or GLuc2) of *Gaussia princeps* luciferase to generate Supt4h-GL1 and NGN-GL2. In the assay, luciferase activity should only be detectable when the two split Gluc subunits are brought into close proximity by the interaction of Supt4h and NGN (FIG. 6A). To control the expression of the two fused proteins, we used an inducible gene expression system, RheoSwitch (FIG. 6B, New England Bio.). The RheoSwitch system requires a cell line expressing RheoSwitch ligand (RSL1) receptor. The fusion constructs were placed under the control of a promoter (pNEBR-X1) that is activated by RheoSwitch ligand (RSL1). To test the sensitivity and inducibility of our constructs, HEK-293 cells were transiently co-transfected with pNEBR-R1 with pNEBRX1-supt4h-Gluc1, pNEBRX1-NGN-Gluc2 or both and RSL1 was then added to the cell culture medium at the final concentration of 150 nM. 24 hours after RSL1 addition, cells were washed with PBS and lysed with Gaussia Luciferase lysis/reaction buffer. The Gausssia luciferase substrate, native Coelenterazine, was added at a final concentration of 10 µg/ml to extracts of cells containing the indicated constructs and the magnitude of luminescence was determined using a luminometer (Tecan Infinite M200) that detects light emitted by luciferase. FIG. 6C shows the cellular luciferase activity resulting from RSL1 activation of promoters expressing either Supt4h-G1 or NGN-G2 or both. No luciferase activity is observed in the absence of RSL1 or cells only transfected with one fusion construct. Significant induction of luciferase activity was only detected when the two proteins Supt4h-G1 and NGN-G2 were expressed together under RSL1 stimulation, indicating that the luciferase activity resulted from the interaction of Supt4h and NGN. The luciferase activity that is detected is very specific and results only from interaction between the Supt4h and NGN. FIG. 6D showed either Supt4-G1 or NGN-G2 with other protein linked to G2 does not produce luciferase activity. One point mutation on NGN (S214F on human Supt5h, corresponding to S324F on yeast Spt5) can inhibit formation of a Supt4h/5h complex and abolish the luciferase activity mediated by Supt4h/NGN interaction.

Before we performed the high throughput screening with the small molecule compound library containing 130,000 compounds, we made a HEK-293 cell clone (293R1) which was engineered to constitutively express RSL1 receptor by selecting cloned cells from cells transfected with pNEBR-R1 plasmid. We also modified the above mentioned reporter system. Gausssia luciferase, a highly sensitive reporter but catalyzing light emission with a short half-life, was modified with two amino acid substitutions (M43I and M110I) according to "A high-throughput cell-based Gausssia luciferase reporter assay for identifying modulators of fibulin-3 secretion" published on J Biomol Screen. 2013 July; 18(6):647-58) to generate a reporter with much more stable light emission. In order to ensure the expression of the two fusion proteins at similar levels, both Supt4h-GLuc1 and NGN-GLuc2, under their own inducible promoter, were placed into one pNEBRX1 plasmid. The construct was then introduced into 293R1. After antibiotic selection, a cell clone M2-8, which displayed more than 15 fold luciferase signal upon induction, was selected for later compound library screening and confirmation.

Figure 7:
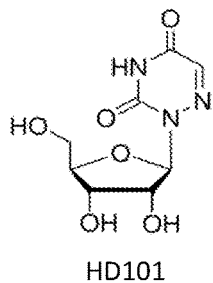
FIGS. 7A to 7D illustrates the inhibition effect of various candidate nucleosides on the luciferase signal resulting from interaction between Supt4h and NGN. Stable cell line M2-8 is a HEK-293 cell clone made to simultaneously express Supt4h-GL1 and NGN-GL2 upon RheoSwitch ligand stimulation. Using this cell line, a high throughput screening for small molecule compounds that can interrupt interaction between Supt4h and NGN was performed. Several candidate nucleosides were found to reduce the Gluc activity mediated by Supt4h/NGN interaction (FIGS. 7A to 7D). The concentrations of the indicated nucleosides were shown at the horizontal axis. In all the experiments, RSL1 concentration was 150 nM. All the experiments were repeated at least twice.
Figure 7:
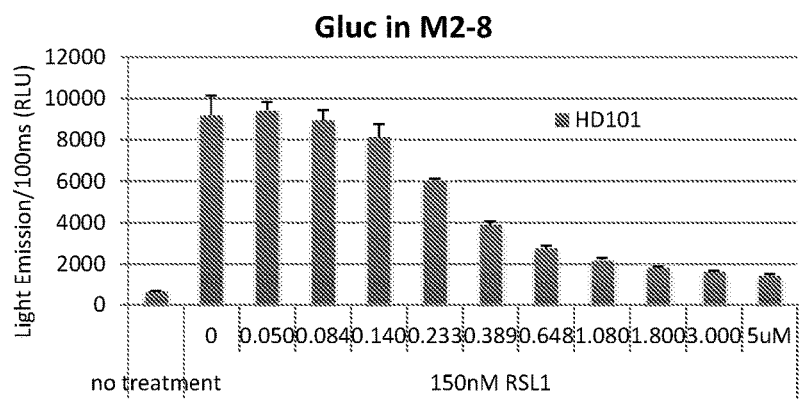
Figure 7:
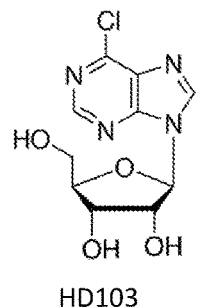
Figure 7:
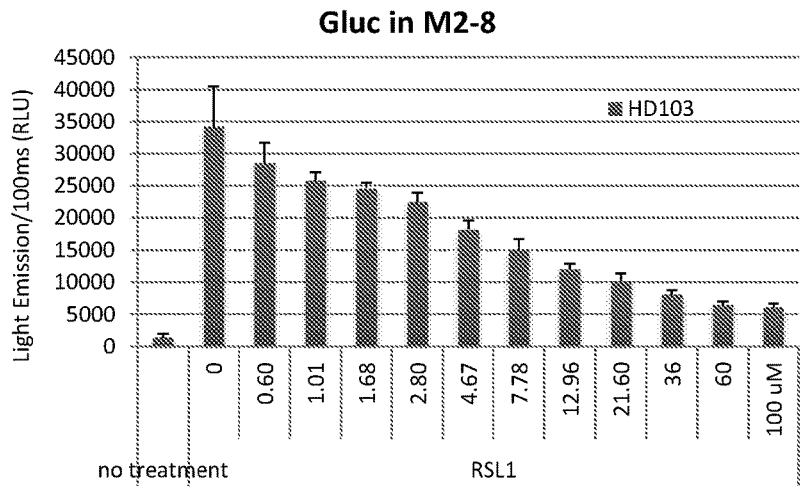
Figure 7:
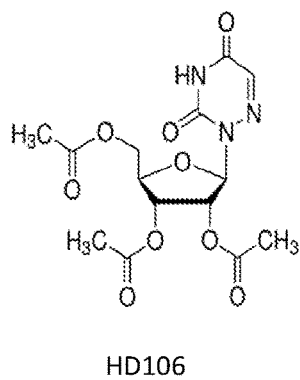
Figure 7:
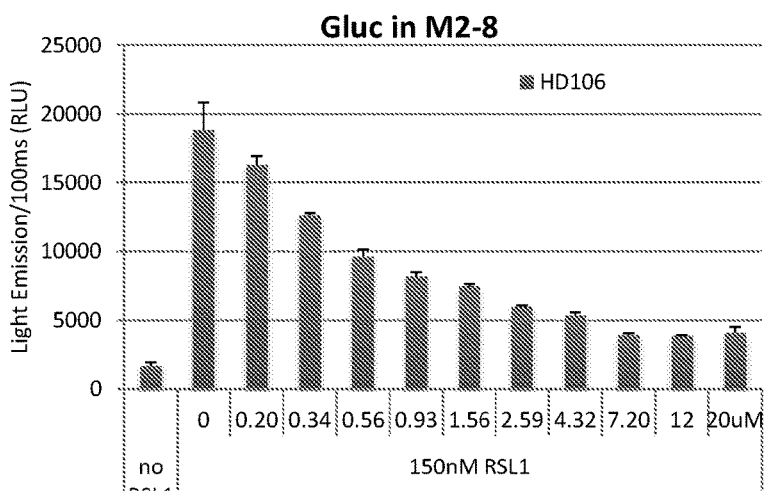
Figure 7:
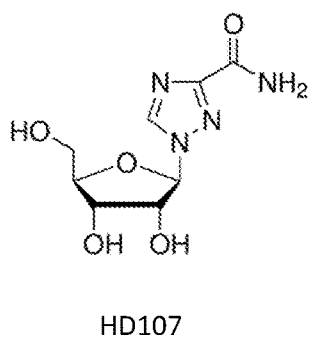
Figure 7:
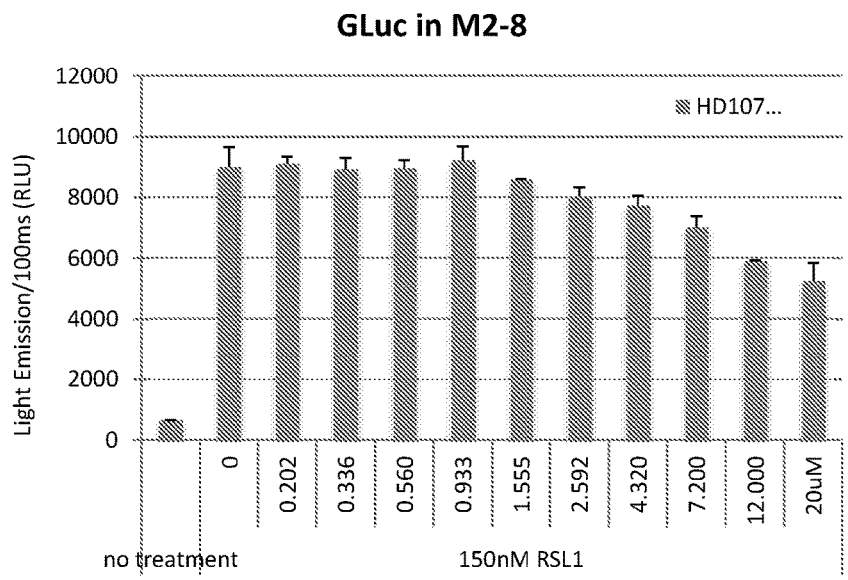

For the library screening, 5000 cells in 20 µl culture medium were seeded into each well of a white 384 well plate. 16 hours later, 10 µl of medium with 150 nM RSL1 were added to each well, and then compounds were added at a final concentration of 10 µM. After 24 hours of incubation, the plates were removed from the incubator, and the culture media were removed by dumping and spinning. The plates were immediately put into a minus 20° C. freezer overnight. To determine the luciferase activity, the frozen plates were combined with 20 µl/well of GLuc lysis buffer (30 mM Tris-HCl pH8.0, 5 mM NaCl, 0.1% Triton X-100 with 10 µg/ml native Coelenterazine) immediately after taking them out from freezer, left in the dark for 1 hr at room temperature, then shaken for 1.5 min in the dark. Luciferase signal was measured by a luminometer (Tecan Infinite M200). After a first round of screening with 130,000 small molecule compounds, 1008 compounds which showed equal to or greater than 50% inhibition in the luciferase activity were selected for further analysis via an 8 point dose response test and the cell toxicity of these compounds was also evaluated. 331 compounds showed little toxicity or at least 2 fold lower IC50 than LC50. Among the candidate compounds, 6-azauridine was identified. Form the above-mentioned independent BiFC screening, 6-CR, another nucleoside was also identified. Combining screening of both, we tested various nucleosides. The result showed various degrees of inhibition in the luciferase activity and that some chemical modifications can reduce the inhibition effect (FIG. 7 A-D)

II. Impact of 6-Azauridine on PolyQ Protein Expression

A. HD101 Preferentially Decreases the Expression Level of Green Fluorescent Protein (GFP) with Amino-Terminal End of Long polyQ To test if the nucleoside 6-Azauridine (HD-101) which has been confirmed for its ability in inhibiting the interaction between Supt4h/NGN through the previous reported two independent systems, YFP based bimolecular fluorescence complementation assay (BiFc) and Gaussia luciferase based protein complementation assay (PCA), can differentially impact the expression of protein with different poly Q length, we have established a fluorescence reporter system which enables the quantitation of the polyQ protein expression directly with a fluorescent microscope.

Figure 8:
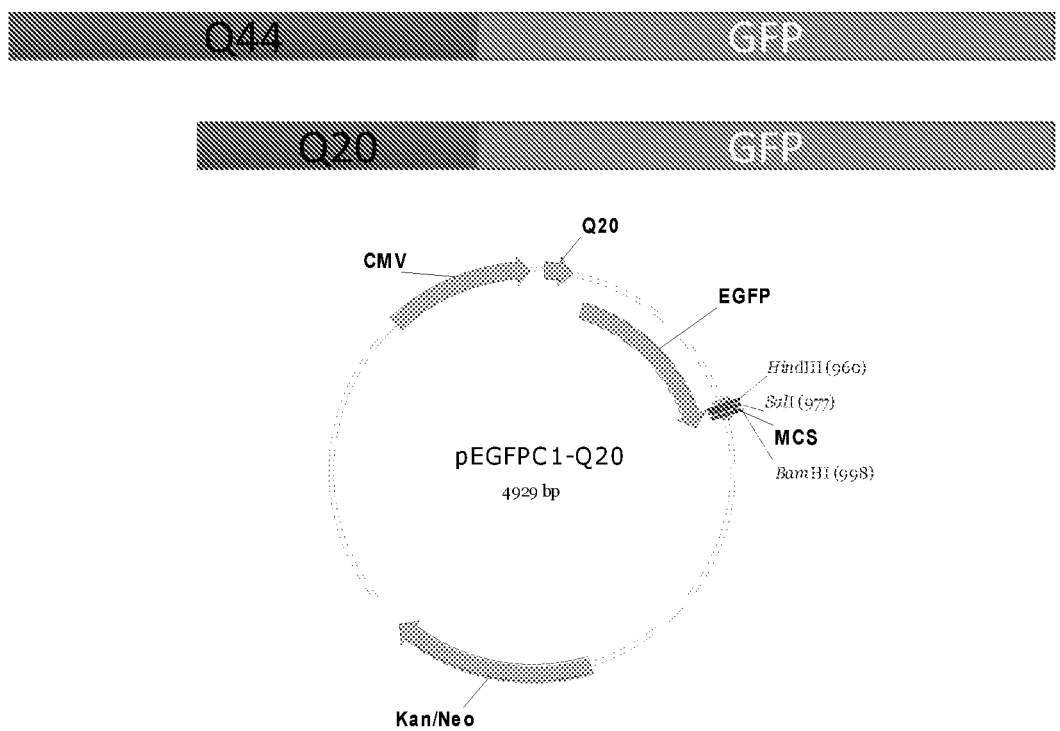
FIGS. 8A to 8B. Poly Q tagged GFP provides a system to examine the specific effect of nucleosides in down regulating a protein with mutated/long poly Q.
Figure 8:
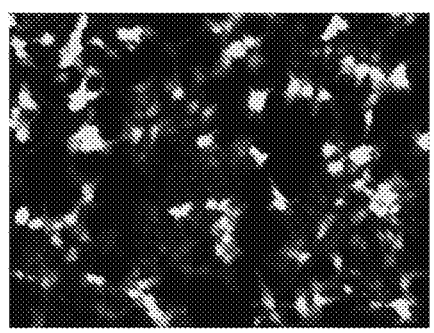
Figure 8:
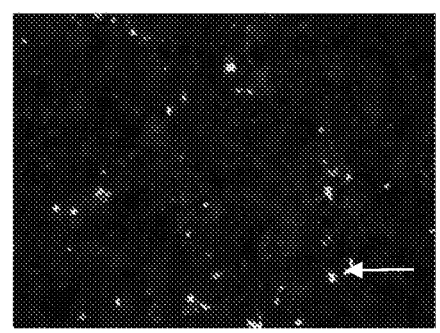

Normal length of poly Q (Q20) and pathogenic length of poly Q(Q44) were in-frame fused at the amino-terminus of eGFPC1 protein to generate Q44- and Q20-GFP (FIG. 8A). The plasmid carrying the polyQ tagged GFP was transfected into HEK 293 cells with greater than 90% transfection efficiency. 48 hours after transfection, protein aggregates were observed in the cells transfected with Q44-GFP (FIG. 8B) while there were no protein aggregates observed in the cells transfected with Q20-GFP, even after an extended period of time of cell culturing (data not shown), indicating the polyQ tagged GFP constructs have the same protein character as Htt with different lengths of polyQ.

Figure 9:
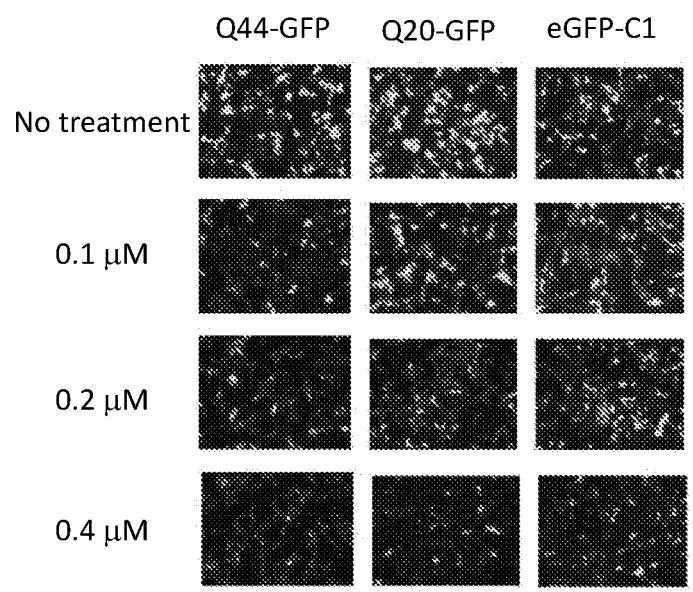
FIGS. 9A to 9B. The effect of HD101 in preferentially reducing the expression of green fluorescence protein (GFP) tagged with long poly-glutamine (pEGFPC1-Q44).
Figure 9:
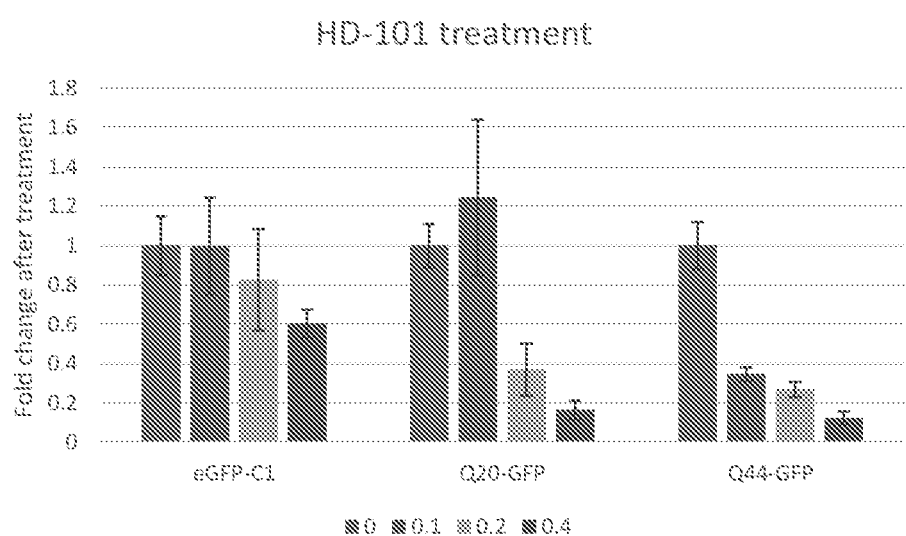

HEK293 cells were transiently transfected with the above mentioned GFP constructs. Five hours after transfection, cells were split among the wells of a 24-well plate and various concentrations of HD101 were added into the wells. 48 hours after transfection, cells were washed with PBS, fixed with 4% paraformaldehyde, and then nuclear stained with DAPI. The cell images were taken by fluorescent microscope (FIG. 9A) and the GFP and DAPI intensity of each field were quantitated using software Image Pro 6.2. After quantitation, the results showed that HD101, while down regulating both Q20 and Q44-GFP significantly and having minimum effect in eGFPC1 expression at the higher concentration, only down regulates Q44-GFP at the low concentration (FIG. 9B). The results show that HD101 preferentially affects the expression of a protein containing a pathological length of polyQ without affecting expression of the other protein.

Figure 10:
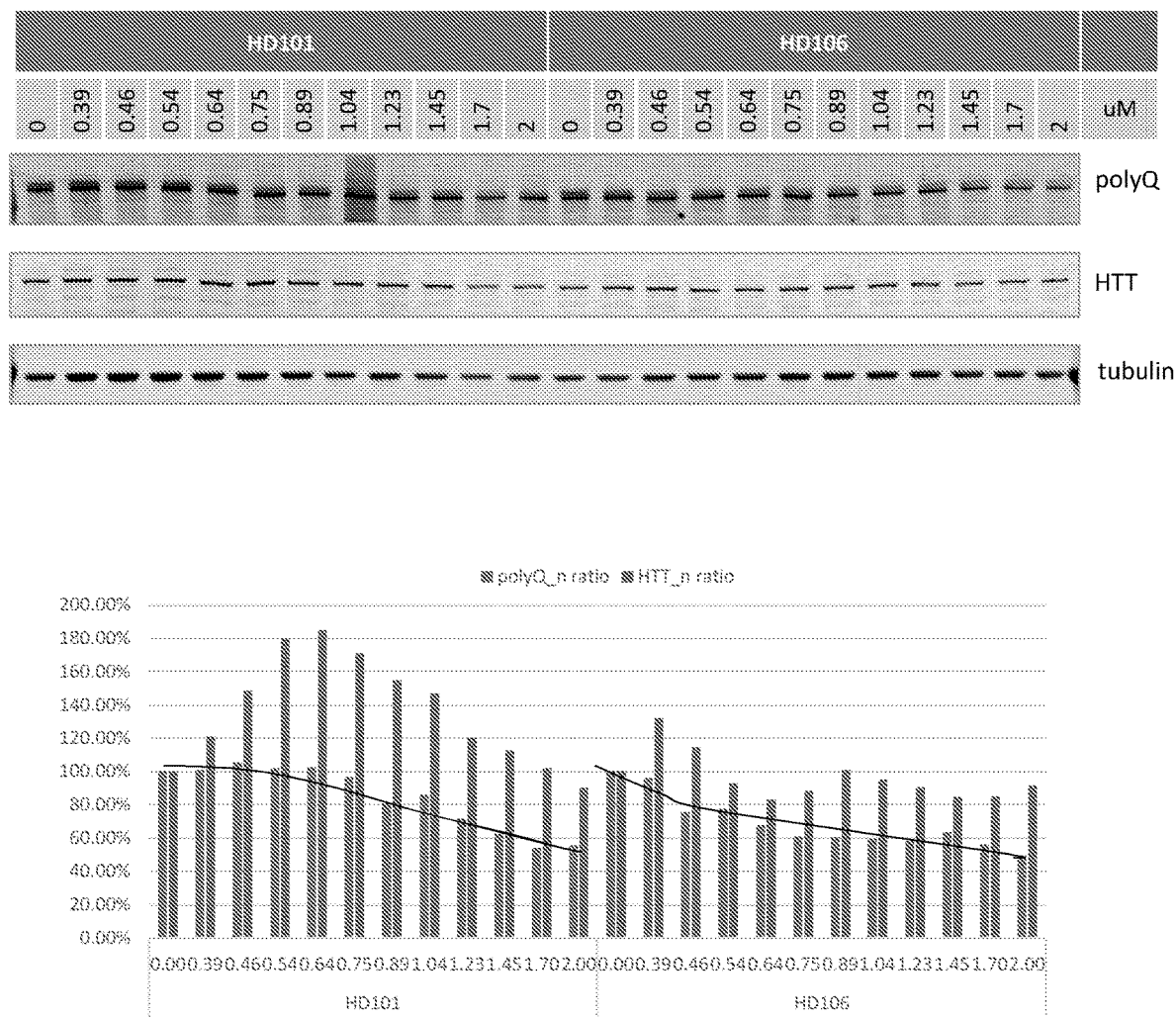
FIG. 10. HD101 and HD106 reduced mutant huntingtin expression in a dose dependent manner in iPSC derived from a Huntington's disease patient. The iPSC were plated in a 24 well plate and treated with HD101 and HD106 at indicated concentration. 24 hr later, the cells were lysed and the protein concentration were determined. Equal amount of protein were loaded onto a 4-12% Bis-Tris protein gel for Western Blot. Anti-poly glutamine antibody, anti-HTT antibody and anti-tubulin antibodies were used to detect endogenous mutant HTT, total HTT and tubulin. The membranes were scanned and the bands were quantified using the Odyssey imaging system from Li-Cor.

B. HD101 and HD106 Preferentially Decrease the Expression Level of Endogenous Mutant Huntingtin Protein To test whether the nucleoside 6-Azauridine (HD101) and (−)-6-Azauridine 2',3',5'-triacetate (HD106) can affect the expression of proteins with long polyQ domains, one iPSC (induced pluripotent stem cell) line ND36999, which was derived from a Huntington's disease patient who carries one allele of mutant htt gene with 180 CAG repeats, was purchased from the Coriell Institute. The iPSCs were plated into a 24-well plate coated with Matrigel. After the cells grew to about 70% confluency, HD101 or HD106 were added at the indicated concentration. After 24 hr, the cells were washed with PBS and the plate was frozen at minus 20° C. overnight. Cells were lysed and the protein concentrations were determined by BCA assay. Equal amounts of protein were loaded onto a protein gel for Western Blot with antibodies recognizing mutant HTT, total HTT and tubulin. The image (FIG. 10) was taken and the quantification was made by Li-Cor Odyssey imaging system. The results showed that both HD101 and HD106 were able to preferentially decrease mutant Huntingtin protein in a dose dependent manner with little effect to total Hungtingtin protein expression level.

Notwithstanding the appended clauses, the disclosure is also defined by the following clauses:

1. A method of reducing the deleterious impact of a target gene in a cell, the method comprising:
    contacting a cell with an effective amount of a nucleoside agent that reduces the deleterious impact in the cell of a target gene comprising a mutant extended nucleotide repeat (NR) domain.
2. The method according to Clause 1, wherein nucleoside agent reduces expression of a toxic expression product of the target gene.
3. The method according to Clause 2, wherein the toxic expression product is a ribonucleic acid expression product.
4. The method according to Clause 2, wherein the toxic expression product is a mutant protein.
5. The method according to any of Clauses 2 to 4, wherein the nucleoside agent differentially reduces expression of the toxic expression product.
6. The method according to Clause 5, wherein the toxic expression product is a mutant protein.
7. The method according to Clause 6, wherein the amount of protein encoded by a mutant allele of the target gene in the cell decreases relative to the amount of the protein encoded by the normal allele of the gene.
8. The method according to Clause 1, wherein the mutant extended NR domain is present in a coding region of the gene.
9. The method according to Clause 1, wherein the mutant extended NR domain is present in a non-coding region of the gene.
10. The method according to any of the preceding clauses, wherein the mutant extended NR domain is a mutant trinucleotide repeat (TNR) domain.
11. The method according to Clause 10, wherein the mutant extended TNR domain is a CAG repeat domain.
12. The method according to Clause 11, wherein the mutant extended TNR domain comprises 35 or more CAG repeats.
13. The method according to Clause 10, wherein the mutant extended TNR domain is a CTG repeat domain.
14. The method according to Clause 13, wherein the mutant extended trinucleotide repeat domain comprises 26 or more CTG repeats.
15. The method according to Clause 10, wherein the mutant extended TNR domain is a CGG repeat domain.
16. The method according to Clause 10, wherein the mutant extended TNR domain is a GCC repeat domain.
17. The method according to Clause 10, wherein the mutant extended TNR domain is a GAA repeat domain.
18. The method according to any of Clauses 1 to 8 or Clause 10, wherein the target gene is selected from the group consisting of: ataxin 1, ataxin 2, ataxin 3, ataxin 7, TBP, atrophin 1, androgen receptor protein and huntingtin protein (HTT) genes.
19. The method according to Clause 18, wherein the gene is an HTT gene.
20. The method according to any of Clauses 1 to 9, wherein the mutant extended NR domain is a mutant extended hexanucleotide domain.
21. The method according to Clause 20, wherein the mutant extended hexanucleotide domain is GGGGCC.
22. The method according to any of the preceding clauses, wherein the nucleoside agent modulates a function of a SPT4 protein in the cell.
23. The method according to Clause 22, wherein the nucleoside agent diminishes interaction of the SPT4 protein and a second protein.
24. The method according to Clause 23, wherein the second protein is a SPT5 protein.
25. The method according to Clause 24, wherein the nucleoside agent diminishes interaction between Supt4h and Supt5h.
26. The method according to Clause 25, wherein the nucleoside agent diminishes interaction between Supt5h and RNA Polymerase II.
27. The method according to any of the preceding clauses, wherein the cell is in vitro.
28. The method according to any of Clauses 1 to 26, wherein the cell is in vivo.
29. The method according to Clause 28, wherein the method comprises:
    administering the nucleoside agent to a subject that includes the cell.
30. The method according to Clause 29, wherein the subject is a mammal.
31. The method according to any of Clauses 29 or 30, wherein the subject is suffering from a disease condition and the method modifies progression of the disease condition.
32. The method according to Clause 31, wherein the method modulates a symptom of the disease condition.
33. The method according to Clause 32, wherein the method modulates a surrogate marker of the disease condition.
34. The method according to any of Clauses 29 to 33, further comprising:
    administering concomitantly or in sequence a second active agent.
35. The method according to Clause 1, wherein the nucleoside agent is a compound or prodrug thereof described by the formula:

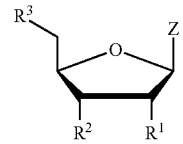

wherein:
    $R^1$, $R^2$ and $R^3$ are independently selected from H, halogen, OH, acyloxy, alkoxy, substituted alkoxy, a phosphorus containing group, thiol, thioalkoxy, substituted thioalkoxy, azido, amino, aminoacyloxy and substituted amino; and
    Z is selected from a purine or a pyrimidine, or an analog thereof.
36. The method according to Clause 1, wherein the nucleoside agent is a ribonucleoside agent or prodrug thereof.
37. The method according to Clause 36, wherein the nucleoside agent is selected from a 6-deazapurine ribonucleoside and a 6-azauridine ribonucleoside or prodrugs thereof.

38. The method according to Clause 37, wherein the 6-deazapurine ribonucleoside is described by the formula:

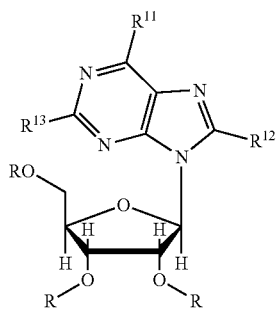

wherein:
each R is independently selected from, H, acyl, aminoacyl, alkyl, substituted alkyl, a phosphorus containing group and an enzymatically cleavable group; and
$R^{11}$, $R^{12}$ and $R^{13}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

39. The method according to Clause 38, wherein each R is independently H or acyl, $R^{11}$ is halogen and $R^{12}$ and $R^{13}$ are hydrogen.

40. The method according to Clause 37, wherein the 6-azauridine ribonucleoside is described by the formula:

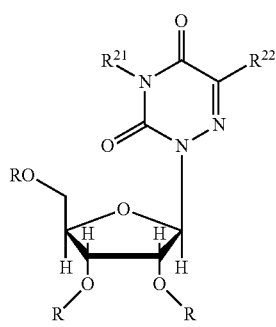

wherein:
each R is independently selected from, H, acyl, aminoacyl, alkyl, substituted alkyl, a phosphorus containing group and an enzymatically cleavable group; and
$R^{21}$ and $R^{22}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

41. The method according to Clause 40, wherein each R is independently H or acyl, $R^{21}$ is hydrogen and $R^{22}$ is hydrogen.

42. The method according to Clause 37, wherein the ribonucleoside agent is selected from one of the following structures:

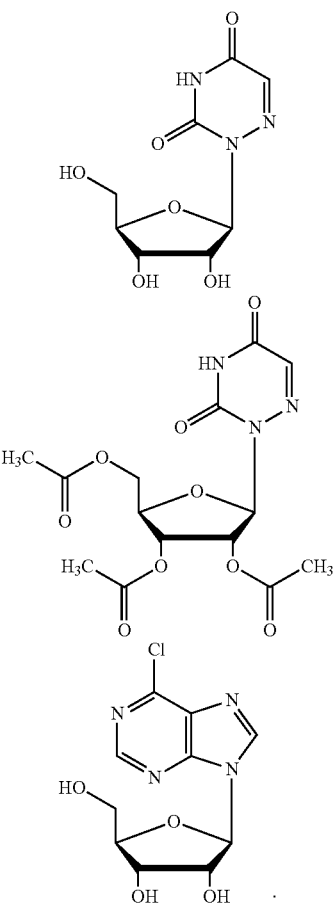

43. A method of diminishing interaction of a SPT4 protein and a SPT5 protein in a sample, the method comprising:
contacting the sample with an effective amount of a nucleoside agent that selectively diminishes the interaction of the SPT4 protein and the SPT5 protein.

44. The method according to Clause 43, wherein the nucleoside agent diminishes interaction between Supt4h and Supt5h.

45. The method according to Clause 43, wherein the nucleoside agent is a ribonucleoside agent or prodrug thereof.

46. The method according to Clause 43, wherein the sample comprises a cell.

47. The method according to Clause 43, wherein the cell is in vitro.

48. The method according to Clause 43, wherein the cell is in vivo.

49. A kit, comprising:
 a nucleoside agent; and
 a second active agent.

50. The kit according to Clause 49, wherein the nucleoside agent is a compound or prodrug thereof described by the formula:

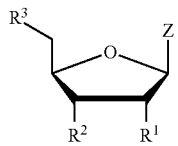

wherein:
 $R^1$, $R^2$ and $R^3$ are independently selected from H, halogen, OH, acyloxy, alkoxy, substituted alkoxy, a phosphorus containing group, thiol, thioalkoxy, substituted thioalkoxy, azido, amino, aminoacyloxy and substituted amino; and
 Z is selected from a purine or a pyrimidine, or an analog thereof.

51. The kit according to Clause 50, wherein the nucleoside agent is a ribonucleoside agent or prodrug thereof.

52. The kit according to Clause 51, wherein the nucleoside agent is selected from a 6-deazapurine ribonucleoside and a 6-azauridine ribonucleoside or prodrug thereof.

53. The kit according to Clause 52, wherein the 6-deazapurine ribonucleoside is described by the formula:

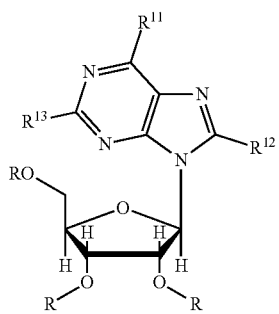

wherein:
 each R is independently selected from, H, acyl, aminoacyl, alkyl, substituted alkyl, a phosphorus containing group and an enzymatically cleavable group; and
 $R^{11}$, $R^{12}$ and $R^{13}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl.

54. The kit according to Clause 53, wherein each R is independently H or acyl, $R^{11}$ is halogen and $R^{12}$ and $R^{13}$ are hydrogen.

55. The kit according to Clause 52, wherein the 6-azauridine ribonucleoside is described by the formula:

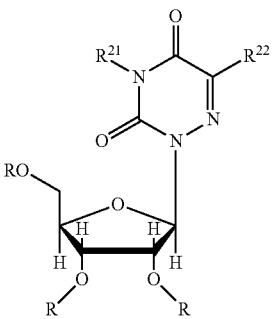

wherein:
 each R is independently selected from, H, acyl, aminoacyl, alkyl, substituted alkyl, a phosphorus containing group and an enzymatically cleavable group; and
 $R^{21}$ and $R^{22}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO₂-alkyl, —SO₂-substituted alkyl, —SO₂-aryl, —SO₂-heteroaryl and trihalomethyl.

56. The kit according to Clause 55, wherein each R is independently H or acyl, $R^{21}$ is hydrogen and $R^{22}$ is hydrogen.

57. The kit according to Clause 52, wherein the ribonucleoside agent or prodrug thereof is selected from one of the following structures:

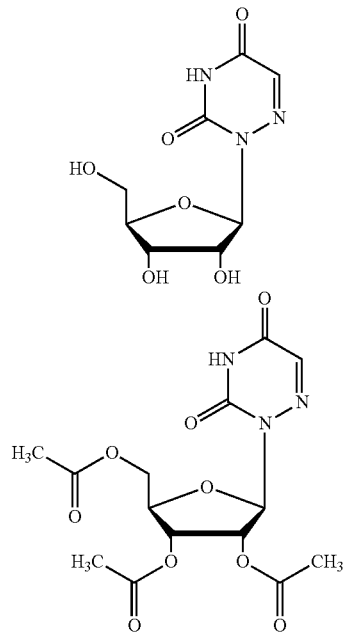

-continued

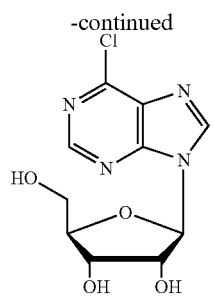

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing the deleterious impact of a target gene in a cell, the method comprising:
contacting a cell with an effective amount of a nucleoside agent that reduces the deleterious impact in the cell of a target gene comprising a mutant extended nucleotide repeat (NR) domain, wherein the nucleoside agent is a compound or prodrug thereof described by the formula:

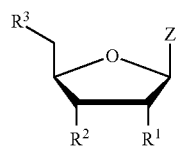

wherein:
$R^1$, $R^2$ and $R^3$ are independently selected from H, halogen, OH, acyloxy, alkoxy, substituted alkoxy, thiol, thioalkoxy, substituted thioalkoxy, azido, amino, aminoacyloxy and substituted amino; and
Z is selected from a purine, an azauracil, a purine analog and a pyrimidine analog, wherein if Z is a purine or a purine analog, the 6-position of the purine is not an amino or substituted amino substituent.

2. The method according to claim 1, wherein the nucleoside agent reduces expression of a toxic expression product of the target gene.

3. The method according to claim 2, wherein the toxic expression product is a ribonucleic acid expression product.

4. The method according to claim 2, wherein the toxic expression product is a mutant protein.

5. The method according to claim 2, wherein the nucleoside agent differentially reduces expression of the toxic expression product.

6. The method according to claim 1, wherein the mutant extended NR domain is a mutant trinucleotide repeat (TNR) domain.

7. The method according to claim 1, wherein the target gene is selected from the group consisting of: ataxin 1, ataxin 2, ataxin 3, ataxin 7, TBP, atrophin 1, androgen receptor protein and huntingtin protein (HTT) genes.

8. The method according to claim 7, wherein the gene is an HTT gene.

9. The method according to claim 1, wherein the nucleoside agent modulates a function of a SPT4 protein in the cell.

10. The method according to claim 1, wherein the nucleoside agent is a ribonucleoside agent or prodrug thereof.

11. The method according to claim 10, wherein the nucleoside agent is selected from a compound of formula (II), or a compound of formula (III):

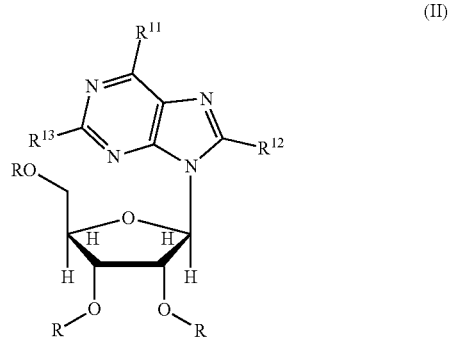

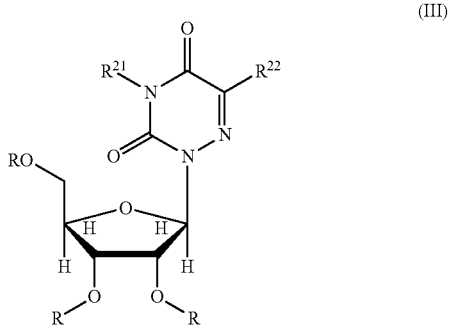

wherein:
each R is independently selected from, H, acyl, aminoacyl, alkyl, substituted alkyl, and an enzymatically cleavable group; and
$R^{11}$, $R^{12}$, $R^{13}$, $R^{21}$ and $R^{22}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl, wherein $R^{11}$ is not an amino or a substituted amino.

12. A method of diminishing interaction of a SPT4 protein and a SPT5 protein in a sample, the method comprising:

contacting the sample with an effective amount of a nucleoside agent that diminishes the interaction of the SPT4 protein and the SPT5 protein, wherein the nucleoside agent is a compound or prodrug thereof described by the formula:

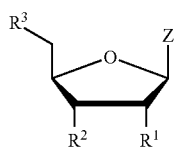

wherein:

$R^1$, $R^2$ and $R^3$ are independently selected from H, halogen, OH, acyloxy, alkoxy, substituted alkoxy, thiol, thioalkoxy, substituted thioalkoxy, azido, amino, aminoacyloxy and substituted amino; and Z is selected from a purine, an azauracil, a purine analog and a pyrimidine analog, wherein if Z is purine or a purine analog, the 6-position of the purine is not an amino or substituted amino substituent.

13. The method according to claim 12, wherein the nucleoside agent diminishes interaction between Supt4h and Supt5h.

14. The method according to claim 12, wherein the nucleoside agent is a ribonucleoside agent or prodrug thereof.

15. The method according to claim 12, wherein the nucleoside agent is selected from a compound of formula (II), or a compound of formula (III):

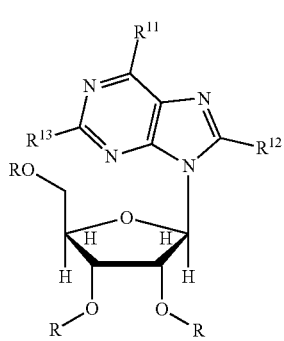

(II)

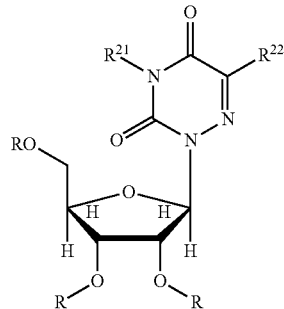

(III)

wherein:

each R is independently selected from, H, acyl, aminoacyl, alkyl, substituted alkyl, and an enzymatically cleavable group; and $R^{11}$, $R^{12}$, $R^{13}$, $R^{21}$ and $R^{22}$ are independently selected from the group consisting of: H, halogen, alkyl, substituted alkyl, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl, wherein $R^{11}$ is not an amino or a substituted amino.

16. The method according to claim 11, wherein the nucleoside agent is selected from one of the following structures:

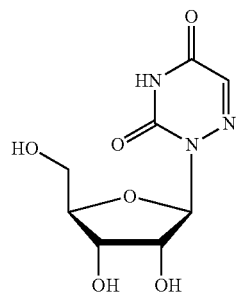

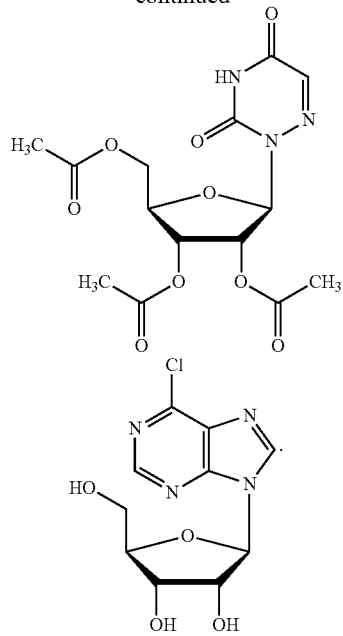

17. The method according to claim 15, wherein the nucleoside agent is selected from one of the following structures:

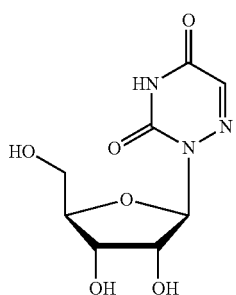

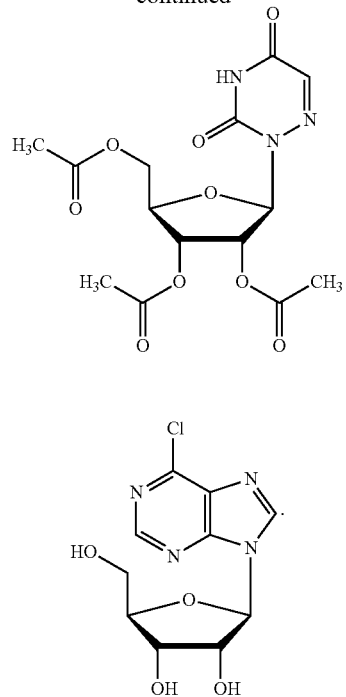

18. The method of claim 1, wherein the nucleoside agent reduces the deleterious impact in the cell of the target gene by 2-fold or more, compared to a target gene in a cell not treated with the nucleoside agent.

19. The method of claim 12, wherein the nucleoside agent diminishes the interaction of the SPT4 protein and the SPT5 protein in the sample by 2-fold or more, compared to a sample not contacted with the nucleoside agent.

20. The method of claim 4, wherein the amount of protein encoded by a mutant allele of the target gene in the cell decreases relative to the amount of the protein encoded by the normal allele of the gene.

* * * * *